(12) United States Patent
Sharp et al.

(10) Patent No.: US 11,519,027 B2
(45) Date of Patent: Dec. 6, 2022

(54) SINGLE-CELL RNA SEQUENCING USING CLICK-CHEMISTRY

(71) Applicant: Massachusetts Institute of Technology, Cambridge, MA (US)

(72) Inventors: Phillip A. Sharp, Cambridge, MA (US); Dig Mahat, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 666 days.

(21) Appl. No.: 16/368,957

(22) Filed: Mar. 29, 2019

(65) Prior Publication Data
US 2019/0390266 A1  Dec. 26, 2019

Related U.S. Application Data

(60) Provisional application No. 62/650,838, filed on Mar. 30, 2018.

(51) Int. Cl.
*C12Q 1/6869* (2018.01)
*C12Q 1/6855* (2018.01)
*C12Q 1/686* (2018.01)

(52) U.S. Cl.
CPC .......... *C12Q 1/6869* (2013.01); *C12Q 1/686* (2013.01); *C12Q 1/6855* (2013.01); *C12Q 2563/149* (2013.01); *C12Q 2563/185* (2013.01); *C12Q 2600/166* (2013.01); *C12Y 207/01078* (2013.01)

(58) Field of Classification Search
CPC .... C12Q 1/6869; C12Q 1/6855; C12Q 1/686; C12Q 2563/185; C12Q 1/6806; C12Y 207/01078
See application file for complete search history.

(56) References Cited

U.S. PATENT DOCUMENTS

| | | | |
|---|---|---|---|
| 6,399,335 B1 * | 6/2002 | Kao | C12P 19/34 435/6.1 |
| 2011/0263688 A1 * | 10/2011 | Barany | A61P 35/00 536/23.1 |
| 2013/0046083 A1 * | 2/2013 | Brown | C07H 1/00 536/23.1 |
| 2015/0051113 A1 * | 2/2015 | Kim | C07H 21/04 506/16 |
| 2016/0145683 A1 * | 5/2016 | Fan | C12Q 1/6874 506/16 |

FOREIGN PATENT DOCUMENTS

WO   WO 2013/013820 A1   1/2013

OTHER PUBLICATIONS

Samanta et al, 2013, Amodified dinucleotide for site-specific RNA-labelling by transcription priming and click chemistry, 2014, 50, pp. 1313-1316, Published Online (Year: 2014).*
Bao et al, Capturing the interactome of newly transcribed RNA, 2018, Nature Methods, 15, 213-220, published online Feb. 12, 2018. (Year: 2018).*
Cutler et al, Polyvalent Oligonucleotide Iron Oxide Nanoparticle "Click" Conjugates, 2010, NanoLett., 10, 1477-1480 (Year: 2010).*
Thompson et al, Oligonucleotide and Polymer Functionalized Nanoparticles for Amplification-Free Detection of DNA, 2012, Biomacromolecules, 13, 1981-1989. (Year: 2012).*
Invitation to Pay Additional Fees dated Jul. 23, 2019, for Application No. PCT/US2019/024736.
Anhauser et al., Enzyme-mediated tagging of RNA. Curr Opin Biotechnol. Dec. 2017;48:69-76. doi: 10.1016/j.copbio.2017.03. 013. Epub Apr. 8, 2017.
Chen et al., Reverse transcription through a bulky triazole linkage in RNA: implications for RNA sequencing. Chem Commun (Camb). Jul. 21, 2014;50(57):7597-600. doi: 10.1039/c4cc03027c.
Delehanty et al., Active cellular sensing with quantum dots: transitioning from research tool to reality; a review. Anal Chim Acta. Oct. 31, 2012;750:63-81. doi: 10.1016/j.aca.2012.05.032. Epub May 26, 2012.
Jao et al., Exploring RNA transcription and turnover in vivo by using click chemistry. Proc Natl Acad Sci USA. Oct. 14, 2008;105(41):15779-84. doi: 10.1073/pnas.0808480105. Epub Oct. 7, 2008.
Winz et al., Nucleotidyl transferase assisted DNA labeling with different click chemistries. Nucleic Acids Res. Sep. 30, 2015;43(17):e110, 10 pages. doi: 10.1093/nar/gkv544. Epub May 26, 2015.

* cited by examiner

*Primary Examiner* — Narayan K Bhat
(74) *Attorney, Agent, or Firm* — Wolf, Greenfield & Sacks, P.C.

(57) ABSTRACT

The present disclosure relates to a method of sequencing nascent RNA in a cell. In some embodiments, the nascent RNA is conjugated to DNA using copper-catalyzed azide-alkyne cycloaddition (CuAAC). Methods of the present disclosure can be used to generate genomic libraries of a cell and measure gene expression and enhancer and/or super-enhancer activity.

19 Claims, 18 Drawing Sheets

| | | 1 | 2 | 3 | 4 | 5 | 6 |
|---|---|---|---|---|---|---|---|
| run-on | ATP, GTP, UTP | ✓ | ✓ | ✓ | ✓ | ✓ | ✓ |
| | CTP | ✓ | - | - | - | - | - |
| | 3'O-Propargyl-CTP | - | ✓ | ✓ | ✓ | ✓ | ✓ |
| | Sarkosyl | 0.025% | 0.025% | 0.025% | 0.025% | 0% | 0.5% |
| CuAAC | Cy5-azide | ✓ | ✓ | - | ✓ | ✓ | ✓ |
| | CuSO$_4$ | ✓ | ✓ | ✓ | ✓ | ✓ | ✓ |
| | Sodium ascorbate | ✓ | ✓ | ✓ | - | ✓ | ✓ |

Cy5 channel

FIG. 2A

| RNA-Propargyl (19 bp) | 2 | 2 | 2 |
| [gamma-32P]-ATP | 3 | 3 | 3 |
| PNK | 2 | 2 | - |
| | | | |
| azide-sc-beads | 2 | 2 | 2 |
| CuSO$_4$ | 3 | 3 | 3 |
| Sodium ascorbate | - | 8 | 8 |
| | | | |

SINGLE-CELL RNA SEQUENCING USING CLICK-CHEMISTRY

RELATED APPLICATION

This application claims priority under 35 U.S.C. § 119(e) to U.S. provisional patent application No. 62/650,838, filed Mar. 30, 2018, the entire contents of which are incorporated herein by reference.

GOVERNMENT SUPPORT

This invention was made with Government support under Grant Nos R01 GM034277, R01 CA133404 and P01 CA042063 awarded by the National Institutes of Health. The Government has certain rights in the invention.

FIELD

Methods and compositions for sequencing nascent RNA from a cell using click-chemistry are disclosed herein.

BACKGROUND

The mammalian genome is pervasively transcribed. Of the 3 billion base pairs in the human genome, only about 1.5% encode proteins and the majority of the rest are associated with non-coding RNA molecules, long interspersed nuclear elements (LINEs), short interspersed nuclear elements (SINEs), introns, and regulatory elements (e.g., enhancers, super-enhancers, insulators). Regulatory elements control transcription of protein-coding genes and the amount of RNA transcribed from the regulatory elements reflects their activity. The protein-coding RNA is processed (e.g., poly-adenylation at the 3' end), which confers stability. However, the RNA transcribed from regulatory elements is unprocessed (e.g., no poly-adenylation at the 3' end) and thus unstable and rapidly degraded. One approach to study regulatory elements and their role in gene expression is to capture, sequence, and analyze nascent RNA transcribed from active regulatory elements. Nascent RNA are unprocessed RNA associated with transcribing RNA polymerase, and they are produced from all transcribed regions of the genome irrespective of function and protein coding potential. Measurement of nascent RNA reports the position, orientation, and amount of transcriptionally engaged RNA polymerases, hence the transcription, at protein-coding genes, non-coding genes, and regulatory elements simultaneously. Previous methods for sequencing RNA from single cells rely on the presence of the poly-adenylated tail at the 3' end of the processed RNA and will not capture unprocessed, unstable, and rapidly degraded nascent RNA.

SUMMARY

The present disclosure is based on development of a method for sequencing all nascent RNA in a single cell using azide-alkyne cycloaddition (AAC). Nascent RNA refers to all RNA that are in the process of being transcribed by RNA polymerase. Some cellular RNA sequencing techniques rely on isolation of mature RNA that has been processed (e.g., poly-A tail). These techniques do not detect nascent RNA, which are unprocessed (e.g., no poly-A tail) and rapidly degraded upon release from the RNA polymerase. Small RNA sequencing methods that do not rely on poly-A tail also fail to capture nascent RNA due to their underrepresentation in the steady-state RNA pool of a cell because of their instability. Thus, because methods of the present disclosure sequence all nascent RNA in a cell, these methods allow detecting and measuring transcription of protein-coding genes, non-coding genes, and activity of regulatory elements (e.g., enhancers, super-enhancers, insulators).

In some aspects, methods for analyzing nascent RNA are provided. The methods include labeling nascent RNA in one or more permeabilized cells or nuclei by incubating the one or more permeabilized cells or nuclei with either alkyne-NTPs or azide-NTPs, which are incorporated into nascent RNA transcripts by RNA polymerases in the one or more permeabilized cells or nuclei; providing bead-bound azide-labeled single-cell barcode-adaptors if the one or more permeabilized cells or nuclei are incubated with alkyne-NTPs, or providing bead-bound alkyne-labeled singe-cell barcode-adaptors if the one or more permeabilized cells or nuclei are incubated with the azide-NTPs; and contacting the lysate of the one or more permeabilized cells or nuclei with the bead-bound azide-labeled single-cell barcode-adaptor or the bead-bound alkyne-labeled single-cell barcode-adaptor in the presence of a copper-catalyzed azide-alkyne cycloaddition (CuAAC) reaction reagent, forming RNA-single-cell-barcoded-adaptor conjugates. The methods optionally include sequencing the nascent RNA or measuring the level of RNAs by quantitative PCR (qPCR).

In some aspects, methods for analyzing nascent RNA are provided. The methods include labeling nascent RNA in one or more permeabilized cells or nuclei by incubating the one or more permeabilized cells or nuclei with either alkyne-NTPs or azide-NTPs, which are incorporated into nascent RNA transcripts by RNA polymerases in the one or more permeabilized cells or nuclei; providing free azide-labeled single-cell barcode-adaptors if the one or more permeabilized cells or nuclei are incubated with alkyne-NTPs, or providing free alkyne-labeled single-cell barcode-adaptors if the one or more permeabilized cells or nuclei are incubated with the azide-NTPs; and contacting the lysate of the one or more permeabilized cells or nuclei with the free azide-labeled single-cell barcode-adaptors or the free alkyne-labeled single-cell barcode-adaptors in the presence of a copper-catalyzed azide-alkyne cycloaddition (CuAAC) reaction reagent, forming RNA-single-cell-barcoded-adaptor conjugates. The methods optionally include sequencing the nascent RNA or measuring the level of RNAs by quantitative PCR (qPCR).

In some embodiments of the foregoing methods, the azide group is at or near the 5'-end of the bead-bound single-cell barcode-adaptors or the free single-cell barcode-adaptors.

In some embodiments of the foregoing methods, the sequencing comprises annealing a reverse transcription primer to the bead-bound single-cell barcode-adaptors or free single-cell barcode-adaptors, and contacting the annealed reverse transcription primer with a polymerase to reverse transcribe the nascent RNA through an adduct formed by the CuAAC reaction. In some embodiments, the adduct is a triazole ring.

In some embodiments, the methods also include incorporating a second adaptor, optionally on the other end of the RNA, thereby forming a single-cell barcode-adaptor hybrid. In some embodiments, the incorporation of the second adaptor is by a template-switching oligonucleotide or ligation.

In some embodiments of the foregoing methods, the nascent RNA is sequenced from a single permeabilized cell or nucleus. In other embodiments of the foregoing methods, the nascent RNA is sequenced from a plurality of permeabilized cells or nuclei.

In some embodiments of the foregoing methods, the CuAAC reaction reagent is copper sulfate (CuSO4), tetrakis(acetonitrile)copper(I)hexafluorophosphate ((Cu(CH3CN)4]PF6), tetrakis(acetonitrile)copper(I) triflate (Cu(CH3CN)4]OTf, copper acetate ($C_4H_6CuO_4$), copper bromide (BrCu), or copper iodide (CuI).

In some embodiments of the foregoing methods, a reducing reagent reduces Cu(II) to Cu(I) in the CuAAC reaction. In some embodiments, the reducing agent is sodium ascorbate, hydrazine, tris(2-carboxyethyl)phosphine (TCEP), dithiothreitol (DTT), or beta-mercaptoethanol.

In some embodiments of the foregoing methods, the CuAAC reaction is in the presence of an accelerating ligand. In some embodiments, the accelerating ligand is 2-[4-({bis[(1-tert-butyl-1H-1,2,3-triazol-4-yl)methyl]amino}methyl)-1H-1,2,3-triazol-1-yl]acetic acid (BTTAA), (1-(4-methoxybenzyl)-1-H-1,2,3-triazol-4-yl)methanol (MBHTM), or tris-hydroxypropyltriazolylmethylamine (THPTA).

In some embodiments of the foregoing methods, the CuAAC reaction is in the presence of a releasing agent. In some embodiments, the releasing agent is urea.

In some embodiments of the foregoing methods, the methods further include sorting the one or more permeabilized cells or nuclei into single wells or encapsulated into aqueous droplets in oil emulsion.

In some aspects, modified rNTP are provided wherein the ribose or the nucleotide base comprises an alkyne conjugated to: the second carbon of the ribose sugar, the third carbon of the ribose sugar, the sixth carbon of the nitrogenous base, the eighth carbon of the nitrogenous base, the alpha phosphate, the beta phosphate, or the gamma phosphate. In some embodiments, the modified rNTP is rATP, rCTP, rUTP, and/or rGTP.

In some aspects, modified rNTPs are provided wherein the ribose of the nucleotide base comprises an azide conjugated to: the second carbon of the ribose sugar, the third carbon of the ribose sugar, the sixth carbon of the nitrogenous base, the eighth carbon of the nitrogenous base, the alpha phosphate, the beta phosphate, or the gamma phosphate. In some embodiments, the modified rNTP is rATP, rCTP, rUTP, and/or rGTP.

In some aspects, plurality of bead-bound single-cell barcode-adaptors is provided. The plurality of bead-bound single-cell barcode-adaptors includes i) oligonucleotides bound to beads; and ii) an azide group conjugated at or near the 5' end of the oligonucleotides. In some embodiments, the oligonucleotides bound to the beads comprise the same nucleotide sequence. In other embodiments, the oligonucleotides bound to the beads do not comprise the same nucleotide sequence.

In some aspects, a plurality of bead-bound single-cell barcode-adaptors is provided. The plurality of bead-bound single-cell barcode-adaptors includes i) oligonucleotides bound to beads; and ii) an alkyne conjugated at or near the 5' end of the oligonucleotides. In some embodiments, the oligonucleotides bound to the beads comprise the same nucleotide sequence. In other embodiments, the oligonucleotides bound to the beads do not comprise the same nucleotide sequence.

In some aspects, a plurality of free single-cell barcode-adaptors is provided. The plurality of free single-cell barcode-adaptors includes i) oligonucleotides; and ii) an azide group conjugated at or near the 5' end of the oligonucleotides. In some embodiments, the oligonucleotides of the free single-cell barcode-adaptors comprise the same nucleotide sequence. In other embodiments, the oligonucleotides of the free single-cell barcode adaptors do not comprise the same nucleotide sequence.

In some aspects, a plurality of free single-cell barcode-adaptors is provided. The plurality of free single-cell barcode-adaptors includes i) oligonucleotides; and ii) an alkyne conjugated at or near the 5' end of the oligonucleotides. In some embodiments, the oligonucleotides bound to the free single-cell barcode-adaptors comprise the same nucleotide sequence. In other embodiments, the oligonucleotides bound to the free single-cell barcode-adaptors do not comprise the same nucleotide sequence.

In some aspects, methods for analyzing nascent RNA are provided. The methods include labeling nascent RNA in one or more permeabilized cells or nuclei by incubating the one or more permeabilized cells or nuclei with azide-NTPs, which are incorporated into nascent RNA transcripts by RNA polymerases in the one or more permeabilized cells or nuclei; providing bead-bound alkyne-labeled single-cell barcode-adaptors; and contacting a lysate of the one or more permeabilized cells or nuclei with the bead-bound alkyne-labeled single-cell barcode-adaptors in the presence of a strain-promoted azide-alkyne cycloaddition (SPAAC) reaction reagent, forming RNA-single-cell-barcoded-adaptor conjugates. The methods optionally include sequencing the nascent RNA or measuring the level of RNAs by quantitative PCR (qPCR).

In some aspects, methods for analyzing nascent RNA are provided. The methods include labeling nascent RNA in one or more permeabilized cells or nuclei by incubating the one or more permeabilized cells or nuclei with azide-NTPs, which are incorporated into nascent RNA transcripts by RNA polymerases in the one or more permeabilized cells or nuclei; providing free alkyne-labeled single-cell barcode-adaptors; and contacting a lysate of the one or more permeabilized cells or nuclei with the free alkyne-labeled single-cell barcode-adaptors in the presence of a strain-promoted azide-alkyne cycloaddition (SPAAC) reaction reagent, forming single-cell barcode adaptor conjugates. The methods optionally include sequencing the nascent RNA or measuring the level of RNAs by quantitative PCR (qPCR).

In some embodiments of the foregoing methods, the sequencing comprises annealing a reverse transcription primer to the bead-bound single-cell barcode-adaptors or free single-cell barcode-adaptors, and contacting the annealed reverse transcription primer with a polymerase to reverse transcribe the nascent RNA through an adduct formed by the SPAAC reaction. In some embodiments, the adduct is a triazole ring.

In some embodiments of the foregoing methods, the methods further include incorporating a second adaptor, optionally on the other end of the RNA, thereby forming a single-cell barcode-adaptor hybrid. In some embodiments, the incorporation of the second adaptor is by a template-switching oligonucleotide or ligation.

In some embodiments of the foregoing methods, the nascent RNA is sequenced from a permeabilized single cell or nucleus. In other embodiments of the foregoing methods, the nascent RNA is sequenced from a plurality of permeabilized cells or nuclei.

In some embodiments of the foregoing methods, the alkyne is bicyclo[6.1.0]nonyne (BCN), N-[(1R,8S,9s)-bicyclo[6.1.0]non-4-yn-9-ylmethyloxycarbonyl]-1,8-diamino-3,6-dioxaoctane, (1R,8S,9s)-bicyclo[6.1.0]non-4-yn-9-yl-methanol, or [(1R,8S,9s)-bicyclo[6.1.0]non-4-yn-9-ylmethyl N-succinimidyl carbonate.

In some aspects, methods for analyzing RNAs in a permeabilized cell or nucleus are provided. The methods include oxidizing 3-terminal cis-diol groups of RNA to dialdehyde; conjugating an alkyne to the dialdehyde by reductive amination by contacting the dialdehyde with a primary amine to form an imine intermediate and reducing the imine to amine using a reducing reagent; and isolating the RNAs. The methods optionally include sequencing the RNAs or measuring the level of RNAs by quantitative PCR (qPCR). In some embodiments, the reducing reagent is cyanoborohydride, sodium borohydride, formic acid, or palladium on carbon (PD/c).

In some aspects, methods for analyzing RNAs in a permeabilized cell or nucleus are provided. The methods include transferring an azide or an alkyne group to the gamma (γ) phosphate on the 5' end of the RNAs; and isolating the RNAs. The methods optionally include sequencing the RNAs; or measuring the level of RNAs by quantitative PCR (qPCR). In some embodiments, the transferring is catalyzed by polynucleotide kinase. In some embodiments, the transferring is by ligation or hybridization of a small oligonucleotide containing azide or alkyne.

In some aspects, methods for locating enhancers and/or super-enhancers in a permeabilized cell or nucleus are provided. The methods include oxidizing 3'-terminal cis-diol groups of RNA in the permeabilized cell or nucleus to dialdehyde; conjugating an alkyne group to the dialdehyde by reductive amination by contacting the dialdehyde with a primary amine to form an imine intermediate and reducing the imine to amine using a reducing reagent; isolating the RNAs; sequencing the isolated RNAs; and
aligning the sequenced isolated RNAs to a reference genome, wherein enhancers and/or super-enhancers are located upstream or downstream of transcribed genes. In some embodiments, the reducing reagent is cyanoborohydride, borohydride, formic acid, or palladium on carbon (PD/c).

In some aspects, methods for locating enhancers and/or super-enhancers in a permeabilized cell or nucleus are provided. The methods include transferring an azide or an alkyne group to the gamma (γ) phosphate on the 5' end of RNAs in the permeabilized cell or nucleus; isolating the RNAs; sequencing the isolated RNAs; and aligning the sequenced isolated RNAs to a reference genome, wherein enhancers and/or super-enhancers are located upstream or downstream of transcribed genes. In some embodiments, the transferring is catalyzed by polynucleotide kinase. In some embodiments, the transferring is by ligation or hybridization of a small oligonucleotide containing azide or alkyne.

In some aspects, methods for measuring enhancer and/or super-enhancer activity in a permeabilized cell or nucleus are provided. The methods include oxidizing 3'-terminal cis-diol groups of RNA in the permeabilized cell or nucleus to dialdehyde; conjugating an alkyne group to the dialdehyde by reductive amination by contacting the dialdehyde with a primary amine to form an imine intermediate and reducing the imine to amine using a reducing reagent to form labeled RNAs; isolating the labeled RNAs; sequencing the isolated RNAs; and measuring the level of RNAs by quantitative PCR (qPCR). In some embodiments, the reducing reagent is cyanoborohydride, borohydride, formic acid, or palladium on carbon (PD/c).

In some aspects, methods for measuring enhancer and/or super-enhancer activity in a permeabilized cell or nucleus are provided. The methods include transferring an azide or an alkyne group to the gamma (γ) phosphate on the 5' end of RNAs in the permeabilized cell or nucleus to form labeled RNAs; isolating the labeled RNAs; sequencing the isolated RNAs; and measuring the level of RNAs by quantitative PCR (qPCR). In some embodiments, the transferring is catalyzed by polynucleotide kinase. In some embodiments, the transferring is by ligation or hybridization of a small oligonucleotide containing azide or alkyne.

In some embodiments of the foregoing methods, a higher level of the enhancer and/or super-enhancer activity results in increased RNAs from the genes regulated by the enhancer and/or super-enhancer relative to a control. In other embodiments of the foregoing methods, a lower level of the enhancer and/or super-enhancer activity results in decreased RNAs from the genes regulated by the enhancer and/or super-enhancer relative to a control.

In some aspects, methods of generating a library of nascent RNA sequences in a permeabilized cell or nucleus are provided. The methods include oxidizing a 3'-terminal cis-diol group of nascent RNAs in the permeabilized cell or nucleus to dialdehyde; conjugating an alkyne group to the dialdehyde by reductive amination by contacting the dialdehyde with a primary amine to form an imine intermediate and reducing the imine to amine using a reducing reagent to form labeled RNAs; isolating the labeled RNAs; and conjugating the isolated RNAs to a bead.

In some aspects, libraries are provided. The libraries include the sequences of nascent genomic RNA in a permeabilized cell or nucleus generated by the foregoing method of generating a library.

In some aspects, methods of generating a library of nascent RNA sequences in a permeabilized cell or nucleus are provided. The methods include transferring an azide or an alkyne group to the gamma (γ) phosphate on the 5' end of nascent RNAs in the permeabilized cell or nucleus to form labeled RNAs; isolating the labeled RNAs; and conjugating the isolated RNAs to a bead. In some embodiments, the transferring is catalyzed by polynucleotide kinase. In some embodiments, the transferring is by ligation or hybridization of a small oligonucleotide containing azide or alkyne.

In some aspects, libraries are provided. The libraries include the sequences of nascent genomic RNA in a permeabilized cell or nucleus generated by the foregoing method of generating a library.

In some aspects, methods of generating a library of nascent RNA sequences in a plurality of permeabilized cells or nuclei are provided. The methods include oxidizing a 3'-terminal cis-diol group of nascent RNAs in the permeabilized cells or nuclei to dialdehyde; conjugating an alkyne group to the dialdehyde by reductive amination by contacting the dialdehyde with a primary amine to form an imine intermediate and reducing the imine to amine using a reducing reagent to form labeled RNAs; isolating the labeled RNAs; and conjugating the isolated RNAs to a bead.

In some aspects, libraries are provided. The libraries include the sequences of nascent genomic RNA in a plurality of permeabilized cells or nuclei generated by the method of generating a library.

In some aspects, methods of generating a library of nascent RNA sequences in a plurality of permeabilized cells or nuclei are provided. The methods include transferring an azide or an alkyne group to the gamma (γ) phosphate on the 5' end of the RNAs in the permeabilized cell or nucleus to form labeled RNAs; isolating the labeled RNAs; and conjugating the isolated RNAs to a bead. In some embodiments, the transferring is catalyzed by polynucleotide kinase. In some embodiments, the transferring is by ligation or hybridization of a small oligonucleotide containing azide or alkyne.

In some aspects, libraries are provided. The libraries include the sequences of nascent genomic RNA in a plurality of permeabilized cells or nuclei generated by the method of generating a library.

In some aspects, methods for sequencing of nascent RNA in a single permeabilized cell or nucleus are provided. The methods include isolating a single permeabilized cell or nucleus; labeling nascent RNA in the single permeabilized cell or nucleus by incubating the permeabilized cell or nucleus with either alkyne-labeled NTPs or azide-NTPs, which are incorporated into nascent RNA transcripts by RNA polymerase in the single permeabilized cell or nucleus; contacting a lysate of the single permeabilized cell or nucleus with azide-labeled single-cell barcode-adaptors or alkyne-labeled single-cell barcode-adaptors in the presence of a copper-catalyzed azide-alkyne cycloaddition (CuAAC) reaction reagent, forming RNA-single-cell-barcoded-adaptor conjugates; fragmenting the nascent RNA by incubating with zinc chloride at 65° C.; reverse transcribing the nascent RNA into complementary DNA (cDNA); and sequencing the cDNA. In some embodiments of the foregoing methods, the methods further include amplifying the cDNA by PCR to produce a PCR product. In some embodiments of the foregoing methods, the methods further include size-selecting a PCR product by polyacrylamide gel electrophoresis.

In some embodiments of the foregoing methods, the single-cell barcode-adaptors are immobilized on a bead. In some embodiments of the foregoing methods, the single-cell barcode-adaptors are free.

In some embodiments of the foregoing methods, the nascent RNA is sequenced from a plurality of permeabilized cells or nuclei.

In some embodiments of the foregoing methods, the CuAAC reaction reagent is copper sulfate (CuSO4), tetrakis(acetonitrile)copper(I)hexafluorophosphate ((Cu(CH3CN)4]PF6), tetrakis(acetonitrile)copper(I) triflate (Cu(CH3CN)4]OTf, copper acetate ($C_4H_6CuO_4$), copper bromide (BrCu), or copper iodide (CuI).

In some embodiments of the foregoing methods, a reducing reagent reduces Cu(II) to Cu(I) in the CuAAC reaction. In some embodiments, the reducing agent is sodium ascorbate, hydrazine, tris(2-carboxyethyl)phosphine (TCEP), dithiothreitol (DTT), or beta-mercaptoethanol.

In some embodiments of the foregoing methods, the CuAAC reaction is in the presence of an accelerating ligand. In some embodiments, the accelerating ligand is 2-[4-({bis[(1-tert-butyl-1H-1,2,3-triazol-4-yl)methyl]amino}methyl)-1H-1,2,3-triazol-1-yl]acetic acid (BTTAA), (1-(4-methoxybenzyl)-1-H-1,2,3-triazol-4-yl)methanol (MBHTM), or tris-hydroxypropyltriazolylmethylamine (THPTA).

In some aspects, methods of diagnosing a disease or disorder are provided. The methods include analyzing the nascent RNAs from a single permeabilized cell or nucleus according to any of the foregoing methods of analyzing nascent RNA or any of the foregoing methods of sequencing nascent RNA; and a) sequencing the isolated nascent RNAs; or b) measuring the level of isolated nascent RNAs by quantitative PCR (qPCR); and comparing the sequence or level of isolated nascent RNAs to control RNA samples to diagnose a disease or disorder.

In some embodiments of the foregoing methods, the nascent RNA is sequenced from a population of permeabilized cells or nuclei.

In some embodiments of the foregoing methods, the control RNA samples are from a known healthy subject not having a disease or disorder, from a subject known to have a disease or disorder, or from a reference sequence, wherein the reference sequence is known to be associated with a disease or disorder.

In some aspects, methods of identifying a cell type or types are provided. The methods include analyzing the nascent RNAs from a single permeabilized cell or nucleus according to any of the foregoing methods of analyzing nascent RNA or any of the foregoing methods of sequencing nascent RNA; and a) sequencing the isolated nascent RNAs; or b) measuring the level of isolated nascent RNAs by quantitative PCR (qPCR); and comparing the sequence or level of isolated nascent RNAs to control RNA samples to identify the cell type or types.

In some embodiments of the foregoing methods, the nascent RNA is sequenced from a population of permeabilized cells or nuclei.

In some embodiments of the foregoing methods, the control RNA samples are from a subject having known specific cell types, from a subject known not to have specific cell types, or from a reference sequence, wherein the reference sequence is known to be associated with a particular cell type.

In some aspects, methods of identifying the differentiation state of a cell are provided. The methods include analyzing the nascent RNAs from a single permeabilized cell or nucleus according to any of the foregoing methods of analyzing nascent RNA or any of the foregoing methods of sequencing nascent RNA; and a) sequencing the isolated nascent RNAs; or b) measuring the level of isolated nascent RNAs by quantitative PCR (qPCR); and comparing the sequence or level of isolated nascent RNAs to control RNA samples to identify the differentiation state of the cell.

In some embodiments of the foregoing methods, the nascent RNA is sequenced from a population of permeabilized cells or nuclei.

In some embodiments of the foregoing methods, the control RNA samples are from a subject known to have a specific differentiation state, from a subject known to not have a specific differentiation state, or from a reference sequence, wherein the reference sequence is known to be associated with a specific differentiation state.

In some aspects, methods of identifying the activation state of a cell are provided. The methods include analyzing the nascent RNAs from a single permeabilized cell or nucleus according to any of the foregoing methods of analyzing nascent RNA or any of the foregoing methods of sequencing nascent RNA; and a) sequencing the isolated nascent RNAs; or b) measuring the level of isolated nascent RNAs by quantitative PCR (qPCR); and comparing the sequence or level of isolated nascent RNAs to control RNA samples to identify the activation state of the cell.

In some embodiments of the foregoing methods, the nascent RNA is sequenced from a population of permeabilized cells or nuclei.

In some embodiments of the foregoing methods, the control RNA samples are from a subject known to have a specific activation state, from a subject known to not have a specific activation state, or from a reference sequence, wherein the reference sequence is known to be associated with a specific activation state.

These and other aspects of the invention are further described below.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

FIG. 2A shows the incorporation of 3'-O-propargyl-NTPs by native RNA polymerase. 3'-O-propargyl-CTP is incorporated into nascent RNA during a nuclear run-on assay in a nucleus solubilized with sodium lauroyl sarcosinate (Sarkosyl). 3'-O-propargyl nascent RNAs are conjugated to Cy5-azide using Cu(I)-catalyzed Azide Alkyne Cycloaddition (CuAAC), with $CuSO_4$ as the copper source and sodium ascorbate as the reducing agent for conversion of Cu(II) to Cu(I).

DETAILED DESCRIPTION

Figure 1A:
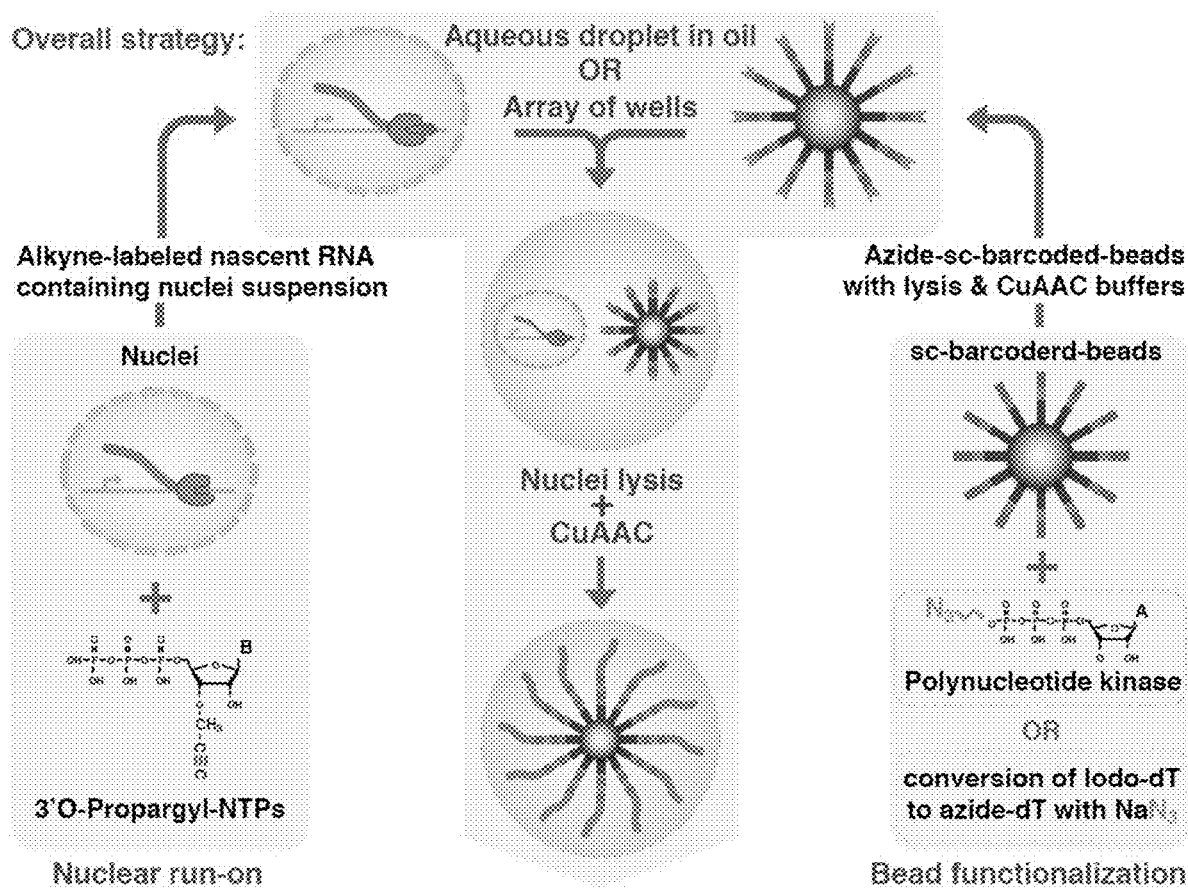
FIGS. 1A-1B show the overall strategies of nascent RNA sequencing in single cells (scGROseq). In bead-based scGROseq, nascent RNAs are labeled with 3'O-propargyl NTPs (3'O-propargyl ATP, 3'O-propargyl CTP, 3'O-propargyl CTP, and/or 3'O-propargyl GTP) containing a terminal alkyne in a nuclear run-on assay. Single-cell (sc) barcoded beads are functionalized with azide at the 5' end of the DNA or RNA either using polynucleotide kinase (PNK) or by conversion of 5' Iodide using sodium azide. Labeled nascent RNAs are conjugated to the functionalized sc-barcoded beads using Cu(I)-catalyzed Azide Alkyne Cycloaddition (CuAAC), forming RNA-single-cell-barcoded-adaptor conjugates (FIG. 1A). In non-bead-based scGROseq, nascent RNAs are labeled with 3'O-propargyl NTPs (3'O-propargyl ATP, 3'O-propargyl CTP, 3'O-propargyl CTP, and/or 3'O-propargyl GTP) containing a terminal alkyne in a nuclear run-on assay. Single nuclei or permeabilized cells are sorted into a 96-well plate or encapsulated into aqueous droplets in oil emulsion. Single cell barcode azide-DNA (azide-DNA), $CuSO_4$, BTTAA, and sodium ascorbate are added to the single nuclei or permeabilized cells in the 96-well plate or droplets. The propargyl-RNA is conjugated to the single cell barcode azide-DNA using CuAAC, forming RNA-single-cell-barcoded-adaptor conjugates. The RNA-single-cell-barcoded-adaptor conjugates are purified. A reverse transcription primer (RT) primer is annealed to the RNA-single-cell-barcoded-adaptor conjugates, forming single-cell barcode-adaptor hybrids. A reverse transcriptase enzyme extends the RT primer into complementary DNA (cDNA) and adds a "CCC" sequence to the 3' end. A template switching oligonucleotide (TSO) containing a "GGG" sequence is annealed to the cDNA, and the TSO is transcribed into cDNA by the reverse transcriptase. The reverse-transcribed complementary DNA (cDNA) is amplified by polymerase chain reaction (PCR). UMI is unique molecular identifier and TSO is template-switching oligonucleotide (FIG. 1B).

The present disclosure provides methods for sequencing nascent RNA. The nascent RNA is labeled and conjugated to single-cell barcode-adaptors utilizing azide-alkyne cycloaddition ("click chemistry"). In addition to providing a sensitive readout on genes and non-coding RNAs that are expressed, these methods can be utilized to locate enhancers and/or super-enhancers in the nascent RNA and to measure enhancer and/or super-enhancer activity in a cell comprising the nascent RNA. The present disclosure also provides methods for generating a library of nascent RNA sequences in a cell or population of cells.

Nascent RNA

RNA is transcribed from DNA in the tightly-regulated process of transcription. Modifications to RNA (e.g., splicing, capping, poly-adenylation), protect the nascent RNA from degradation and regulate down-stream processes such as translation. Nascent RNA is the newly-transcribed RNA that has not been modified. Nascent RNA may be transcribed from a gene, a non-coding sequence, or from a regulatory element.

In some embodiments, nascent RNA is transcribed from a gene. In some embodiments, the gene is a protein coding gene. In some embodiments, the gene is a non-protein coding sequence. Non-coding RNAs are transcribed from non-protein coding sequences. Non-coding RNAs represent about 95% of total RNAs in rapidly growing cells. Non-limiting examples of non-coding RNAs include transfer RNAs (tRNAs), ribosomal RNAs (rRNAs), microRNAs, small interfering RNAs (siRNAs), Piwi-interacting RNAs (piRNAs), small nucleolar RNAs (snoRNAs), small nuclear RNAs (snRNAs), long non-coding RNAs (lncRNAs), and long intergenic non-coding RNAs (lincRNAs).

Regulatory elements are segments of the genome that are capable of increasing or decreasing the expression of specific genes within a subject. Some regulatory elements increase gene expression, and some regulatory elements decrease gene expression. The expression of nascent RNA transcribed from regulatory elements is critical to understanding diseases such as cancer because regulatory elements control the expression of disease-associated genes. For example, regulatory elements stimulate increased transcription of the MYC gene, which is associated with pancreatic cancer, leukemia, and colorectal cancer. Non-limiting examples of regulatory elements include enhancers, super-enhancers, insulators, promoters, and untranslated regions.

In some embodiments, nascent RNA is transcribed from a regulatory element. In some embodiments, the regulatory element is an enhancer. An enhancer is a short (for example, 50-1500 base pair) region of a genome that is bound by transcription factors to increase expression of a particular gene. In some embodiments, the regulatory element is a super-enhancer. A super-enhancer is region of a genome with multiple enhancers that are collectively bound by an array of transcription factor proteins to drive the transcription of genes involved in a cellular pathway. Super-enhancers are bound by higher levels of transcription factors compared with enhancers and are associated with genes that are highly expressed.

Genomic DNA is transcribed into RNA by an RNA polymerase enzyme. Double-stranded DNA is separated and RNA polymerase uses a single strand of the DNA as a template to generate nascent RNA using ribonucleoside triphosphates (rNTPs, e.g., rATP, rUTP, rCTP, rGTP). The present disclosure provides methods for sequencing nascent RNAs by labeling nascent RNAs using modified rNTPs or by labeling nascent RNAs enzymatically (e.g., using PNK), which then can be reacted with a Cu(I)-catalyzed Azide Alkyne Cycloaddition (CuAAC) reagent. A rNTP is a ribose sugar with a nucleoside base conjugated at the 1' carbon of the ribose ring and 3 phosphate groups conjugated at the 5' carbon of the ribose ring. The modified rNTPs are incorporated into the nascent RNA by RNA polymerase and are conjugated to labeled adaptors in the presence of a cycloaddition reaction reagent for sequencing.

The present disclosure provides modified rNTPs for labeling nascent RNA. Labeling refers to incorporating a modified chemical group (e.g., modified rNTP) into a biomolecule. Modified rNTPs have a modification to the ribose sugar, the nucleoside base, and/or the 3 phosphate groups. Non-limiting examples of modifications to rNTPs include 3'-O-alkyne ribose, 3' azide ribose, 2' fluoro ribose, $^{32}$P-γ-phosphate, 2' hydroxyl (OH) ribose, 2'-O-methyl ribose, and 2'-propynyl nucleoside. In some embodiments, the modified rNTPs have a 3'-O-alkyne group instead of a 3'-O-hydroxyl on the ribose sugar. In some embodiments, the modified rNTPs have a 3'-O-azide group instead of a 3'-O-hydroxyl group on the ribose sugar.

Multiple species of modified rNTPs may be utilized to increase the efficiency of labeling nascent RNA. In some embodiments, one modified rNTP is utilized. In some embodiments, two modified rNTPs are utilized. In some embodiments, three modified rNTPs are utilized. In some embodiments, four modified rNTPs are utilized.

Any rNTP may be modified for labeling nascent RNA. In some embodiments, the modified rNTP is ribonucleoside adenosine triphosphate (rATP). In some embodiments, the modified rNTP is ribonucleoside uracil triphosphate (rUTP). In some embodiments, the modified rNTP is ribonucleoside guanosine triphosphate (rGTP). In some embodiments, the modified rNTP is ribonucleoside cytosine triphosphate (rCTP). In some embodiments, the modified rNTP is rATP, rUTP, rGTP, and/or lCTP.

Single-Cell Barcode-Adaptors

The present disclosure provides methods for sequencing RNA using adaptors. An adaptor is an oligonucleotide composed of natural nucleotides, modified nucleotides, and/or synthetic (e.g., non-natural) nucleotides. An adaptor may be composed of DNA nucleotides, RNA nucleotides, RNA and DNA nucleotides (forming a RNA/DNA hybrid), synthetic nucleotides, modified nucleotides, and combinations of two or more of these. An adaptor may be in any conformation known in the art for oligonucleotides. Non-limiting examples of adaptor conformations include single-stranded, double-stranded, a mixture of single-stranded and double stranded, or hairpin-forming. The adaptor may be 15-100 nucleotides in length. In some embodiments, the adaptor is 15-45 nucleotides in length.

In some embodiments, an adaptor comprises a single-cell barcode (hereinafter referred to as "single-cell barcode-adaptors" or "barcode-adaptors"). A single-cell barcode is a sequence of nucleotides, typically up to 20 nucleotides but which can be longer, and is unique to each single cell. A single-cell barcode may be composed of DNA nucleotides, RNA nucleotides, RNA and DNA nucleotides (forming a RNA/DNA hybrid), synthetic nucleotides, modified nucleotides, and combinations of two or more of these. A single-cell barcode may be incorporated into the 5' end of the adaptor. A single-cell barcode may be incorporated into the 3' end of the adaptor. A single-cell barcode may be incorporated into the middle (e.g., not at the 5' end or the 3' end) of the adaptor.

In some embodiments, a single-cell barcode-adaptor oligonucleotide is "bead-bound," i.e., is immobilized on a bead, or other solid object, that is modified to bind nucleotides. In some embodiments, a bead is a microsphere that binds single-cell barcode-adaptors. Beads can be individually assayed or isolated based on the physical characteristics of the bead. Beads for binding single-cell barcode-adaptors may be polystyrene beads, magnetic beads, hydrogel, or silica beads. In some embodiments, the 5' end of the single-cell barcode-adaptor is bound to a bead and the 3' end is not bound to a bead. In some embodiments, the 3' end of the single-cell barcode-adaptor is bound to a bead and the 5' end is not bound to a bead.

In other embodiments, a single-cell barcode-adaptor is not immobilized on a bead (i.e., neither end is bound to a bead), which is also referred to herein as being "free," e.g., a "free single-cell barcode-adaptor."

The single-cell barcode-adaptors may be single-stranded or double-stranded. In some embodiments, the single-cell barcode-adaptors are single-stranded.

In some embodiments, the adaptors contain a unique molecule identifier (UMI) sequence. In some embodiments, the single-cell barcode-adaptors contain a UMI. A UMI is a molecular tag of nucleotides that is used to detect and quantify unique RNA transcripts from a population as opposed to artifacts from PCR amplification (see FIG. 1B). In some embodiments, the UMI sequence is random. A UMI sequence may be 4-30 nucleotides in length. In some embodiments, the UMI is 5-20 nucleotides in length. In some embodiments, the UMI is 6-12 nucleotides in length. In some embodiments, the UMI is 15-30 nucleotides in length.

In some embodiments, methods of sequencing RNA (e.g., nascent RNA) utilize a plurality of single-cell barcode-adaptors molecules (e.g., bead-bound, free). A plurality may include 2 or more single-cell barcode-adaptors molecules, 10 or more single-cell barcode-adaptors molecules, 100 or more single-cell barcode-adaptors molecules, 1,000 or more single-cell barcode-adaptors molecules, 10,000 or more single-cell barcode-adaptors molecules, 100,000 or more single-cell barcode-adaptors molecules, 1,000,000 or more single-cell barcode-adaptors molecules, or 10,000,000 or more single-cell barcode-adaptors molecules. In some embodiments, the plurality of single-cell barcode-adaptors molecules are utilized to sequence the RNA from a single cell. In some embodiments, the plurality of single-cell barcode-adaptors molecules are utilized to sequence the RNA from a plurality of cells.

In some embodiments, single-cell barcode-adaptors molecules (e.g., bead-bound, free) contain an azide group conjugated at or near the 5' end of the adaptor. In some embodiments, the azide group is conjugated at the 5' end of the adaptor. In some embodiments, the azide group is conjugated near the 5' end of the adaptor. As used herein, "near the 5' end" of the adaptor may be 1 nucleotide from the 5' end, 2 nucleotides from the 5' end, 3 nucleotides from the 5' end, 4 nucleotides from the 5' end, 5 nucleotides from the 5' end, 6 nucleotides from the 5' end, 7 nucleotides from the 5' end, 8 nucleotides from the 5' end, 9 nucleotides from the 5' end, 10 nucleotides from the 5' end, 11 nucleotides from the 5' end, 12 nucleotides from the 5' end, 13 nucleotides from the 5' end, 14 nucleotides from the 5' end, 15 nucleotides from the 5' end, 15 nucleotides from the 5' end, 16 nucleotides from the 5' end, 17 nucleotides from the 5' end, 18 nucleotides from the 5' end, 19 nucleotides from the 5' end, or 20 nucleotides from the 5' end.

In some embodiments, single-cell barcode-adaptors molecules (e.g., bead-bound, free) contain an alkyne group conjugated at or near the 5' end of the adaptor. In some embodiments, the alkyne group is conjugated at the 5' end of the adaptor. In some embodiments, the alkyne group is conjugated near the 5' end of the adaptor. As above, "near the 5' end" of the adaptor may be 1 nucleotide from the 5' end, 2 nucleotides from the 5' end, 3 nucleotides from the 5' end, 4 nucleotides from the 5' end, 5 nucleotides from the 5' end, 6 nucleotides from the 5' end, 7 nucleotides from the 5' end, 8 nucleotides from the 5' end, 9 nucleotides from the 5' end, 10 nucleotides from the 5' end, 11 nucleotides from the 5' end, 12 nucleotides from the 5' end, 13 nucleotides from the 5' end, 14 nucleotides from the 5' end, 15 nucleotides from the 5' end, 15 nucleotides from the 5' end, 16 nucleotides from the 5' end, 17 nucleotides from the 5' end, 18 nucleotides from the 5' end, 19 nucleotides from the 5' end, or 20 nucleotides from the 5' end.

The azide or alkyne groups can be conjugated by incorporating labeled nucleotides, such as during synthesis of the single-cell barcode-adaptor molecules, or by enzymatic labeling (e.g., using polynucleotide kinase), or by ligation or hybridization of a small oligonucleotide containing azide or alkyne. In the latter case, a small oligonucleotide can be 3-10 nucleotides in length and includes one or more azide or alkyne labeled nucleotides.

In addition, in other embodiments, single-cell barcode-adaptor molecules are labeled with azide by conversion of 5' Iodide using sodium azide. The labeling of 5'-Iodide in single-cell barcode-adaptor is achieved by either incorporation of Iodine-deoxythymidine at the 5' terminal base using an automated oligo synthesizer or by iodination. Iodination refers to the introduction of iodine (and no other elements) into a molecule. In some embodiments, iodine (and no other elements) is substituted from iodine-deoxythymidine (Iodo-dT) into azide using sodium azide ($NaN_3$), wherein the resulting products are sodium iodide (NaI) and azide-dT. In some embodiments, iodine from Iodo-dT is substituted into into sodium propargylamine.

A plurality of single-cell barcode-adaptors molecules (e.g., bead-bound, free) may comprise the same nucleotide sequence or different nucleotide sequences. In some embodiments, the plurality of single-cell barcode-adaptors molecules comprise the same nucleotide sequence. In some embodiments, the plurality of single-cell barcode-adaptors molecules do not comprise the same nucleotide sequence. In some embodiments, the single-cell barcode-adaptors molecules comprise at least 2 different nucleotide sequences, at least 10 different nucleotide sequences, at least 100 different nucleotide sequences, at least 1,000 different nucleotide sequences, at least 10,000 different nucleotide sequences, at least 100,000 different nucleotide sequences, or any number of different nucleotide sequences between 2-100,000 different nucleotide sequences.

Azide-Alkyne Cycloaddition Reaction

The present disclosure provides methods for sequencing nascent RNA using an azide-alkyne cycloaddition reaction. An azide-alkyne cycloaddition reaction is a chemical reaction in which a molecule with an azide group combines with a molecule with an alkyne group, forming a cyclic adduct. The azide-alkyne cycloaddition reaction catalyzes the conjugation of labeled nascent RNA to complementary, labeled single-cell barcode-adaptors, forming RNA-single-cell-barcoded-adaptor conjugates. Non-limiting examples of azide-alkyne cycloaddition reactions are copper-catalyzed azide-alkyne cycloaddition (CuAAC), strain-promoted azide-alkyne cycloaddition (SPAAC), ruthenium-catalyzed azide-alkyne cycloaddition (RuAAC), silver-catalyzed azide-alkyne cycloaddition (AgAAC), strain-promoted alkyne-nitrone cycloaddition (SPANC).

An azide is a compound with the anion group $N_3^-$ or the $—N_3$ group. An azide group can be utilized to label either nascent RNA or single-cell barcode-adaptors. If the azide group is used to label nascent RNA, the azide group may be conjugated to carbon 2 (C2) or carbon 3 (C3) of the ribose sugar or to carbon 6 (C6) of the uracil or cytosine or carbon 8 (C8) of the adenine or guanosine nitrogenous bases. If the azide group is used to label single-cell barcode-adaptors, the azide group may be conjugated to carbon 2 (C2) or carbon 3 (C3) of the deoxyribose sugar, to carbon 6 (C6) of the thymine or cytosine or carbon 8 (C8) of the adenine or guanosine nitrogenous bases, or to the alpha (α), beta (β), or gamma (γ) phosphates. In some embodiments, the azide is used to label nascent RNA. In some embodiments, the azide is used to label single-cell barcode-adaptors.

Non-limiting examples of azide-containing nucleotides include γ-(2-azidoethyl)-dATP, γ-(2-azidoethyl)-dTTP, γ-(2-azidoethyl)-dCTP, γ-(2-azidoethyl)-dGTP, 8-azido-rATP, 8-azido-rGTP, 6-azido-rCTP, 6-azido-rUTP, 8-azido-dATP, 8-azido-dGTP, 6-azido-dCTP, 6-azido-dTTP, 8-azidoethyl-rATP, 8-azidoethyl-rGTP, 6-azidoethyl-rCTP, 6-azidoethyl-rUTP, 8-azidoethyl-dATP, 8-azidoethyl-dGTP, 6-azidoethyl-dCTP, 6-azidoethyl-dTTP, 8-azidohexyl-rATP, 8-azidohexyl-rGTP, 6-azidohexyl-rCTP, 6-azidohexyl-rUTP, 8-azidohexyl-dATP, 8-azidohexyl-dGTP, 6-azidohexyl-dCTP, and 6-azidohexyl-dTTP.

An alkyne is an unsaturated hydrocarbon containing at least one carbon-carbon triple bond. An alkyne can be utilized to label either nascent RNA or single-cell barcode-adaptors. If the alkyne is used to label nascent RNA, the alkyne group may be conjugated to carbon 2 (C2) or carbon 3 (C3) of the ribose sugar or to carbon 6 (C6) of the uracil or cytosine or carbon 8 (C8) of the adenine or guanosine nitrogenous bases. If the alkyne group is used to label single-cell barcode-adaptors, the alkyne group may be conjugated to carbon 2 (C2) or carbon 3 (C3) of the deoxyribose sugar, to carbon 6 (C6) of the thymine or cytosine or carbon 8 (C8) of the adenine or guanosine nitrogenous bases, or to the alpha (α), beta (β), or gamma (γ) phosphates. In some embodiments, the alkyne is used to label nascent RNA. In some embodiments, the alkyne is used to label single-cell barcode-adaptors.

An alkyne may contain at least two carbons (ethyne), at least three carbons (propyne), at least four carbons (butyne), at least five carbons (pentyne), at least six carbons (hexyne), at least seven carbons (heptyne), at least eight carbons (octyne), at least nine carbons (nonyne), or at least ten carbons (decyne). Alkynes may be straight-chain alkynes or branched alkynes. Non-limiting examples of alkyne-containing nucleotides include 3'-O-propargyl-rATP, 3'-O-propargyl-rUTP, 3'-O-propargyl-CTP, 3'-O-propargyl-rTTP, 3'-O-propargyl-dATP, 3'-O-propargyl-dTTP, 3'-O-propargyl-dGTP, 3'-O-propargyl-dCTP, C8-propargyl-rATP, C8-propargyl-rGTP, C6-propargyl-CTP, C6-propargyl-rUTP, C8-propargyl-dATP, C8-propargyl-dGTP, C6-propargyl-rCTP, C6-propargyl-rUTP, 3'-O-butargyl-rATP, 3'-O-butargyl-rUTP, 3'-O-butargyl-rCTP, 3'-O-butargyl-rTTP, 3'-O-butargyl-dATP, 3'-O-butargyl-dTTP, 3'-O-butargyl-dGTP, 3'-O-butargyl-dCTP, C8-butargyl-rATP, C8-butargyl-rGTP, C6-butargyl-rCTP, C6-butargyl-rUTP, C8-butargyl-dATP, C8-butargyl-dGTP, C6-butargyl-ICTP, and C6-butargyl-rUTP.

In some embodiments, the azide-alkyne cycloaddition reaction is copper-catalyzed azide-alkyne cycloaddition (CuAAC). A CuAAC reaction includes a copper reaction reagent, and may contain a reducing reagent and an accelerating ligand. The copper reaction reagent catalyzes the activation of the alkyne-labeled molecule for combination with the azide-labeled molecule. Non-limiting examples of copper reaction reagents include copper sulfate ($CuSO_4$), tetrakis(acetonitrile)copper(I)hexafluorophosphate (($Cu(CH_3CN)_4)PF_6$), tetrakis(acetonitrile)copper(I)triflate (($Cu(CH_3CN)_4$OTf) copper acetate ($C_4H_6CuO_4$), copper bromide (BrCu), and copper iodide (CuI). In some embodiments, the copper reaction reagents is copper sulfate ($CuSO_4$), tetrakis(acetonitrile)copper(I)hexafluorophosphate (($Cu(CH_3CN)_4)PF_6$), tetrakis(acetonitrile)copper(I)triflate ((Cu(CH$_3$CN)$_4$OTf) copper acetate (C$_4$H$_6$CuO$_4$), copper bromide (BrCu), or copper iodide (CuI).

The reducing reagent catalyzes the reduction of Cu(II) to Cu(I). Non-limiting examples of reducing reagents include sodium ascorbate (C6H7NaO6), hydrazine (N2H4), tris(2-carboxyethyl)phosphine (TCEP), dithiothreitol (DTT), and beta-mercaptoethanol. In some embodiments, the reducing reagent is sodium ascorbate (C6H7NaO6), hydrazine (N2H4), tris(2-carboxyethyl)phosphine (TCEP), dithiothreitol (DTT), or beta-mercaptoethanol.

The accelerating ligand increases the speed of the reaction and also protects the molecules from oxidation. Non-limiting examples of accelerating ligand include 2-[4-({bis[(1-tert-butyl-1H-1,2,3-triazol-4-yl)methyl]amino}methyl)-1H-1,2,3-triazol-1-yl]acetic acid (BTAA), (1-(4-methoxybenzyl)-1-H-1,2,3-triazol-4-yl)methanol (MBHTM), and tris-hydroxypropyltriazolylmethylamine (THPTA). In some embodiments, an accelerating ligand is 2-[4-({bis[(1-tert-butyl-1H-1,2,3-triazol-4-yl)methyl]amino}methyl)-1H-1,2,3-triazol-1-yl]acetic acid (BTAA), (1-(4-methoxybenzyl)-1-H-1,2,3-triazol-4-yl)methanol (MBHTM), or tris-hydroxypropyltriazolylmethylamine (THPTA).

In some embodiments, the azide-alkyne cycloaddition reaction is strain-promoted azide-alkyne cycloaddition (SPAAC). A SPAAC reaction utilizes a strained alkyne derivative. The strained alkyne derivate undergoes a rapid and spontaneous combination with azide-labeled molecule to relieve the strain in the alkyne. Non-limiting examples of alkyne derivatives include bicyclo[6.1.0]nonyne (BCN), N-[(1R,8S,9s)-bicyclo[6.1.0]non-4-yn-9-ylmethyloxycarbonyl]-1,8-diamino-3,6-dioxaoctane, (1R,8S,9s)-bicyclo[6.1.0]non-4-yn-9-ylmethanol, or [(1R,8S,9s)-bicyclo[6.1.0]non-4-yn-9-ylmethyl N-succinimidyl carbonate, difluorooctyne, dibenzylcyclooctyne, and biarylazacyclooctynone. In some embodiments, the cyclooctene derivative is bicyclo[6.1.0]nonyne (BCN), N-[(1R,8S,9s)-bicyclo[6.1.0]non-4-yn-9-ylmethyloxycarbonyl]-1,8-diamino-3,6-dioxaoctane, (1R,8S,9s)-bicyclo[6.1.0]non-4-yn-9-ylmethanol, or [(1R,8S,9s)-bicyclo[6.1.0]non-4-yn-9-ylmethyl N-succinimidyl carbonate.

A cyclic adduct is a structure formed by the azide-alkyne cycloaddition. A cyclic adduct may be formed between nascent RNA and barcode-adaptors. Non-limiting examples of cyclic adducts include triazole, spirocyclic compounds, triazoylmethyl-dialkylamines, triazolyl napththoquinones, triazolylpyridazinones, and triazyl-substituted alkyl phosphonates. In some embodiments, the cyclic adduct is triazole.

In some embodiments, the azide-alkyne cycloaddition reaction is performed in the presence of a releasing agent. A releasing agent is a chemical or compound that promotes the release of labeled nascent RNA from RNA polymerase. Non-limiting examples of releasing agents include urea, protease K, sodium dodecyl sulfate (SDS), TRIzol, guanidine thiocyanate, and guanidine hydrochloride.

In some embodiments, the releasing agent is urea. The urea may be 0.1 molar (M)-10M urea. In some embodiments, the urea is 1M-6 M. In some embodiments, the urea is 3M-8M. In some embodiments, the urea is 5M-10M.

Analyzing RNA

The present disclosure provides methods for analyzing RNA (e.g., nascent RNA). Non-limiting methods for analyzing RNA include sequencing RNAs, measuring the levels of RNA such as by quantitative PCR (qPCR), labeling RNA and mapping its cellular location, and digesting RNA to estimate its accessibility in the nucleus to enzymes.

In some aspects, the present disclosure provides methods for sequencing RNA (e.g., nascent RNA). Sequencing may be by any method known in the art. Non-limiting examples of sequencing include massively parallel signature sequencing (MPSS), polony sequencing, 454 pyrosequencing, Illumina (Solexa) sequencing, combinatorial probe anchor synthesis (cPAS), SOLiD sequencing, Ion Torrent semiconductor sequencing, DNA nanoball sequencing, Heliscope single molecule sequencing, single molecule real time (SMRT) sequencing, Sanger sequencing and nanopore DNA sequencing.

The sequenced RNA (e.g., nascent RNA) may be from a single nucleus or permeabilized cell or from a plurality of nuclei or permeabilized cells. Any cells or nuclei from cells known in the art can be used with methods of the present disclosure. Non-limiting examples of cells include eukaryotic cells or prokaryotic cells. Eukaryotic cells may be mammalian cells (e.g., human, mouse, rat, non-human primate) or non-mammalian cells.

In some embodiments, methods of the present disclosure utilize permeabilized cells. Cells may be permeabilized by any method known in the art, including, but not limited to, utilizing surfactants (e.g., sodium lauroyl sarcosinate, Tween-20, Triton-X), utilizing organic solvents (e.g., methanol, acetone), and heating. In some embodiments, cells are permeabilized using sodium lauroyl sarcosinate (Sarkosyl).

In some embodiments, methods of the present disclosure utilize isolated nuclei. The nuclei may be isolated from cells and/or tissue samples.

Sequencing RNA from a single nucleus or permeabilized cell is critical to understanding the regulation of gene expression and identifying transcription machinery as desirable therapeutic targets. Non-limiting examples of processes that regulate gene expression include transcription bursting, divergent transcription, allelic expression, coordinated transcription, enhancer-promoter coordination, and phase separation. In some embodiments, nascent RNA is sequenced from a single nucleus or permeabilized cell.

Sequencing RNA (e.g., nascent RNA) from a plurality of nuclei or permeabilized cells may help to understand the effects on gene expression on a tissue-level. For example, sequencing RNA from a plurality of nuclei or permeabilized cells is critical to understanding the effect of an exogenous agent (e.g., drug, toxin) on a tissue. A plurality of nuclei or permeabilized cells may be two or more nuclei or permeabilized cells, tens of nuclei or permeabilized cells, hundreds of nuclei or permeabilized cells, thousands of nuclei or permeabilized cells, millions of nuclei or permeabilized cells, billions of nuclei or permeabilized cells, or trillions of nuclei or permeabilized cells. A plurality of nuclei or permeabilized cells may be homogenous or heterogeneous. A homogenous plurality of nuclei or permeabilized cells are all derived from the same cell type, and a heterogeneous plurality of nuclei or permeabilized cells are derived from different cell types. A plurality of nuclei or permeabilized cells may be on a solid culture (e.g. plate), in a liquid culture, in a microfluidic device, in a tissue, or in a sample from a subject (e.g., blood, saliva, sputum). In some embodiments, nascent RNA is sequenced from a plurality of nuclei or permeabilized cells.

In some embodiments, the plurality of nuclei or permeabilized cells are sorted into one or more single nuclei or permeabilized cells prior to sequencing. In some embodiments, the sequencing results from the one or more single nuclei or permeabilized cell are pooled to analyze the results from the plurality of nuclei or permeabilized cells (e.g., tissue). Sorting may be by any method known in the art.

Non-limiting examples of sorting include forward scattered light (FSC) and side scattered light (SSC). In some embodiments, the plurality of cells or nuclei are sorted automatically. Non-limiting examples of devices for automatic sorting include Aria3 FACS sorter (BD Biosciences), WOLF cell sorter (NanoCellect Biomedical), On-chip Sort (On-Chip Biotechnologies), and MoFlo Astrios EQ (Beckman Coulter). In some embodiments, the one or more single nuclei or permeabilized cells are sorted into wells in a microplate. In some embodiments, the one or more single nuclei or permeabilized cells are sorted into wells in a 96-well microplate.

In some embodiments, the one or more single nuclei or permeabilized cells are sorted into droplets prior to sequencing. Once inside the droplets, the one or more single nuclei or permeabilized cell may be lysed to release the RNAs, which are then labeled and conjugated to single-cell barcode-adaptors prior to sequencing. Non-limiting methods of sequencing RNA-barcoded-adaptor conjugates of the present disclosure include dropSEQ, inDrop, single nucleus RNA sequencing (sNuc-Seq), droplet single nucleus RNA sequencing (DroNc-Seq), and the methods comprised in the 10× genomics platform.

RNA (e.g., nascent RNA) may be sequenced after being conjugated to single-cell barcode-adaptor molecules in an azide-alkyne cycloaddition reaction. The RNA is conjugated to the single-cell barcode-adaptor molecules through formation a cyclic adduct (e.g., triazole) between the RNA and the single-cell barcode-adaptors, forming RNA-single-cell-barcoded-adaptor conjugates. In some embodiments, prior to sequencing, a reverse transcription primer is annealed to the single-cell barcode-adaptors. In some embodiments, prior to sequencing, a reverse transcription primer is annealed to RNA (e.g., nascent RNA). Reverse transcription is the synthesis of a DNA template from an RNA molecule or the extension a DNA template from a DNA molecule (e.g., barcode, adaptor). A reverse transcription primer is a short (<50 nucleotide) single strand oligonucleotide that anneals to a target sequence (e.g., single-cell barcode-adaptors).

Reverse transcription is catalyzed by a reverse transcription polymerase, also known as a reverse transcriptase or RNA-dependent DNA polymerase. Non-limiting examples of reverse transcription polymerase include Maxima H Minus (ThermoFisher), Superscript II (Invitrogen), SMARTScribe (ClonTech), Moloney Murine Leukemia Virus (M-MuLV, New England BioLabs), and ProtoScript II (New England BioLabs).

A single cell global run-on sequence reaction (sc-GROseq), as described herein, can be used to generate a library of the RNA (e.g., nascent RNA) from a single cell or a plurality of cells. A library is collection of nucleotide sequences (e.g., DNA, RNA) from a single cell or a plurality of cells. A library may include all of the nucleotide sequences (e.g., RNA) in a single cell or a plurality of cells, or a library may include a subset of the nucleotides sequences in a single cell or a plurality of cells (e.g., nascent RNA).

The RNAs from a scGROseq reaction in a library may be conjugated to a bead. Conjugation can be by any method known in the art. Non-limiting examples of methods of conjugation include reductive amination utilizing carboxylic acid, NHS-ester sulfhydryl cross-linking, biotin-streptavidin linkage, and 1-ethyl-3-(3-dimethylaminopropyl)carbodiimide (EDC) linkage to carboxylated polystyrene beads.

One method of generating a library from nascent RNA is to conjugate labeled nascent RNA with a single-cell barcode-adaptor. The nascent RNA and the single-cell barcode-adaptor may be conjugated using an azide-alkyne cycloaddition reaction. In some embodiments, the nascent RNA is labeled with an azide group and the single-cell barcode-adaptor is labeled with an alkyne group. In some embodiments, the nascent RNA is labeled with an alkyne group and the single-cell barcode-adaptor is labeled with an azide group. In some embodiments, the azide-alkyne cycloaddition reaction is CuAAC. In some embodiments, the azide-alkyne cycloaddition reaction is SPAAC.

In some embodiments, a library is generated from RNA (e.g., nascent RNA) by incorporating a second adaptor into the single-cell barcode-adaptor conjugated to labeled RNA (e.g., nascent RNA), forming a single-cell barcode-adaptor hybrid. The second adaptor may be a template switch oligonucleotide (TSO) that is incorporated by template switching. A TSO anneals to untemplated cytosine nucleotides that are added by the reverse transcription polymerase. Incorporating a TSO into the RNA-single-cell-barcoded-adaptor conjugate ensures that all complementary DNA (cDNA) that is synthesized by the reverse transcription polymerase will have a common sequence that is complementary to the TSO. This common sequence can then be used to PCR amplify the cDNA to generate a library from the RNA (e.g., nascent RNA). In some embodiments, a TSO is incorporated at the 5' end of the RNA-single-cell-barcoded-adaptor conjugate. In some embodiments, a TSO is incorporated at the 3' end of the RNA-single-cell-barcoded-adaptor conjugate.

The second adaptor may also be incorporated into the RNA-single-cell-barcoded-adaptor conjugate using a ligase. A ligase is an enzyme that joins two oligonucleotides (e.g., DNA, RNA) or joins an oligonucleotide with another substance (e.g., protein). Non-limiting examples of ligases include T4 RNA ligase 1, T4 RNA ligase 2, T4 RNA ligase 2-truncated, T4 RNA ligase 2-truncated KQ, RtcB ligase, Blunt/TA DNA ligase, ElectroLigase®, T4 DNA ligase, T3 DNA ligase, T7 DNA ligase, *Thermophilus aquaticus* DNA ligase, 9° N™ DNA ligase, and SplintR® DNA ligase. In some embodiments, the second adaptor is ligated at the 5' end of the RNA-single-cell-barcoded-adaptor conjugate. In some embodiments, the second adaptor is ligated at the 3' end of the RNA-single-cell-barcoded-adaptor conjugate.

The present disclosure provides methods for sequencing all cellular RNAs. All cellular RNAs can be labeled with an azide (e.g., azidoethyl) by reductive amination, or an enzymatic reaction such as using polynucleotide kinase. Reductive amination involves the conversion of a carbonyl group to an amine via an intermediate imine. The 3'-terminal cis-diol group of ribose sugars in rNTPs are oxidized to dialdehydes using an oxidizing reagent.

An oxidizing reagent gains electrons and is reduced in a reaction. Non-limiting examples of oxidizing reagents include sodium periodate (NaIO4), periodic acid (HIO$_4$), and Ru(PPh$_3$)$_3$Cl$_2$/C. An azide (e.g., azidoethyl) can be conjugated to 3'-terminal dialdehydes using primary amines as reducing reagents to form imine intermediates. A reducing reagent loses electrons and is oxidized in a reaction. Imine intermediates may then be reduced to amines using a reducing reagent. Non-limiting examples of primary amines used as reducing reagents include sodium cyanoborohydride (NaBH$_3$CN), sodium borohydride (NaBH$_4$), formic acid (HCO$_2$H), and palladium on carbon (PD/c).

In some embodiments, all cellular RNAs, including nascent RNAs, are labeled using polynucleotide kinase (PNK). PNK is an enzyme that catalyzes the transfer of a gamma (γ) phosphate from ATP to the free hydroxyl (OH) at the 5' DNA or RNA. In some embodiments, the γ-phosphate is labeled with an azide group (e.g., γ-2-azidoethyl-ATP). In some embodiments, the γ-phosphate is labeled with an alkyne group (e.g., γ-2-alkyl-ATP).

The cellular RNAs are isolated prior to sequencing. Any method known in the art may be used to isolate cellular RNAs. Non-limiting examples of isolating RNAs include using TRIzol reagent, sodium dodecyl sulfate (SDS), urea, guanidine thiocynate, and guanidine hydrochloride.

Regulatory elements (e.g., enhancers, super-enhancers) can be located when all cellular RNAs, including nascent RNAs, are sequenced. After the cellular RNAs are labeled by reductive amination as described above, the sequences may be aligned to a reference genome to locate enhancers and/or super-enhancers. Enhancers and super-enhancers may be located upstream of a transcribed gene. Enhancers and super-enhancers may be located downstream of a transcribed gene.

In some aspects, the present disclosure provides methods for measuring the expression of all cellular RNAs, including nascent RNAs. Measuring gene expression can diagnose a disease or disorder, distinguish between cell types, distinguish the differentiation state of cells, and/or distinguish the activation state of cells. Gene expression may be measured by any method known in the art, including, but not limited to, quantitative PCR (qPCR), Northern blot, and fluorescence in situ hybridization (FISH). In some embodiments, gene expression is measured by qPCR. In some embodiments, gene expression is measured from a single cell or permeabilized cell. In some embodiments, gene expression is measured from a population of single nuclei or permeabilized cells.

A higher level of RNAs measured from a specific gene or specific genes compared to a control indicates higher gene expression. A lower level of RNAs measured from a specific gene or specific genes compared to a control indicates lower gene expression. Changes in the level of gene expression may be indicative of a disease or disorder, the type of cell, the differentiation state of the cell, and/or the activation of the cell. A control is a known quantity of cellular RNA. A control may be another cell from the same population, a cell that has not been treated, or a cell of the same type from a different population.

The activity of enhancers and/or super-enhancers can also be measured when all cellular RNAs, including nascent RNAs, are measured Enhancers and super-enhancers stimulate the transcription of genes into RNA, and the activity of enhancers and super-enhancers can be measured by quantitative PCR (qPCR) to measure the levels of total cellular RNA. A higher level of enhancer and/or super-enhancer activity results in increased RNAs from the genes regulated by the enhancer and/or super-enhancer relative to a control. A lower level of the enhancer and/or super-enhancer activity results in decreased RNAs from the genes regulated by the enhancer and/or super-enhancer relative to a control. A control is a known quantity of cellular RNA. A control may be another cell from the same population, a cell that has not been treated, or a cell of the same type from a different population.

Methods of Use

In some aspects, the present disclosure provides methods of diagnosing a disease or disorder comprising analyzing the RNA (e.g., nascent RNA) from a single nucleus or permeabilized cell. Analyzing may be sequencing the RNA and/or measuring the level of RNA. In some embodiments, the RNA is sequenced from a plurality of nuclei or permeabilized cells. Comparing the genes and non-coding sequences that are expressed, the levels of expression, and/or the sequences of the expressed RNAs, to control RNA samples results allows diagnosis of a disease or condition. Control RNA samples may be RNA sequences or levels from a known healthy subject or group of subjects (e.g., not having a disease or disorder), from a subject or group of subjects known to have a disease or disorder, or from a reference sequence, wherein the reference sequence is known to be associated with a disease or disorder.

These diagnostic methods may be particularly applicable in instances where isolating single cells from a tissue is not possible, such as isolating complete neurons from brain or other central nervous system tissue. Methods of the present disclosure allow the isolation of permeabilized cells or nuclei, which can be extracted from tissue samples. These methods therefore allow the diagnosis of diseases or disorders that would previously have been very challenging, given the reliance of other RNA sequencing methods on the isolation of intact single cells.

Non-limiting of diseases or disorders that may be diagnosed using methods of the present disclosure include cancer (e.g., brain cancers, lymphomas, leukemias, lung cancer, pancreatic cancer, breast cancer, renal cancer, prostate cancer, hepatic cancer, gastric cancer, bone cancer), autoimmune disorders (e.g., rheumatoid arthritis, lupus, Celiac disease, Sjogren syndrome), and diabetes.

In some aspects, the present disclosure provides methods of identifying different cell types comprising analyzing the RNA (e.g., nascent RNA) from single nuclei or permeabilized cells. Analyzing may be sequencing the RNA and/or measuring the level of RNA. In some embodiments, the RNA is sequenced from populations of single nuclei or permeabilized cells. Comparing the genes and non-coding sequences that are expressed, the levels of expression, and/or the sequences of the expressed RNAs, to control RNA samples results allows the differentiation of cell types. Control RNA samples may be RNA sequences and expression levels from a subject or group of subjects having known cell types (e.g., tumors, activated T-cells), from a subject or group of subjects known not to have cell types (e.g., tumors, activated T-cells), or from a reference sequence, wherein the reference sequence is known to be associated with a particular cell type.

Non-limiting examples of cell types that may be identified with methods of the instant disclosure include tumors (e.g., solid tumors, serous tumors, brain tumors, spinal cord tumors, meninges tumors, lymphomas, pancreatic tumors, hepatic tumors, breast tumors, renal tumors, lung tumors, gastric tumors, colon tumors, bone tumors, leukemias), T cells (e.g., $CD4^+$, $CD8^+$, regulatory, helper), B cells (e.g., plasma cells, lymphoplasmacytoid cells, memory B cells, B-2 cells, B-1 cells), natural killer cells, stem cells (e.g., hematopoietic).

In some aspects, the present disclosure provides methods of identifying the differentiation state of cells comprising analyzing the RNA (e.g., nascent RNA) from single nuclei or permeabilized cells. Analyzing may be sequencing the RNA and/or measuring the level of RNA. In some embodiments, the RNA is sequenced from populations of single nuclei or permeabilized cells. Comparing the genes and non-coding sequences that are expressed, the levels of expression, and/or the sequences of the expressed RNAs, to control RNA samples results allows the differentiation of cell types. Control RNA samples may be RNA sequences and expression levels from a subject having cells at a known differentiation state (e.g., pluripotent stem cells, partially differentiated, terminally differentiated), from a subject known not to have cell types (e.g., pluripotent stem cells, partially differentiated, terminally differentiated), or from a reference sequence, wherein the reference sequence is known to be associated with a particular differentiation state of a given cell type.

Non-limiting examples of differentiation states that may be identified with methods of the instant disclosure include pluripotent (e.g., embryonic stem cells, induced stem cells), partially differentiated (e.g., hematopoietic stem cells), or terminally differentiated (e.g., neurons, myocytes, osteoblasts, glial cells, epithelial cells).

In some aspects, the present disclosure provides methods of identifying the activation state of cells comprising analyzing the RNA (e.g., nascent RNA) from single nuclei or permeabilized cells. In some embodiments, the RNA is sequenced from populations of single nuclei or permeabilized cells. Analyzing may be sequencing the RNA and/or measuring the level of RNA. In some embodiments, the RNA is sequenced from populations of single nuclei or permeabilized cells. Comparing the genes and non-coding sequences that are expressed, the levels of expression, and/or the sequences of the expressed RNAs, to control RNA samples results allows the differentiation of cell types. Control RNA samples may be RNA sequences and expression levels from a subject or group of subjects having cells at a known activation state (e.g., activated cells, non-activated cells), from a subject or group of subjects known not to have cell types (e.g., activated cells, non-activated cells), or from a reference sequence, wherein the reference sequence is known to be associated with a particular activation state of a given cell type.

Non-limiting examples of activation states that may be identified with methods of the instant disclosure include activated cells (e.g., T cells, B cells, natural killer cells, macrophages, monocytes) and non-activated cells (e.g., senescent cells).

EXAMPLES

Materials and Methods
Sample Preparation.

Samples for single cell Global Run-On & sequencing (scGROseq) should be prepared at 4° C. to avoid unsolicited run-on. All centrifugation steps for sample preparation should be prepared in a cold (4° C.) at 1000 g (unless stated otherwise) for 5 minutes (5 min.). Samples should be prepared by nuclei isolation (A) or cell permeabilization (B).

Nuclei Isolation.
Harvest adherent cells by scraping and centrifuging, non-adherent cells by centrifuging, and tissue samples by dissociating and preparing single-cell suspension.
Resuspend the cell pellet in 10 milliliters (10 mL) ice-cold phosphate buffered saline (PBS) and centrifuge.
Resuspend the cell pellet in ice-cold douncing buffer ($1 \times 10^6$ cells/mL).

TABLE 1

Douncing Buffer Composition

| Douncing buffer reagents | Volume (50 ml) | (5 ml) | Final concentration |
|---|---|---|---|
| DEPC H$_2$O | 33 ml | 3.3 ml | |
| Tris-Cl pH 7.4 (1M) | 500 ul | 50 ul | 10 mM |
| Sucrose (1M) | 15 ml | 1.5 ml | 300 mM |
| CaCl$_2$ (1M) | 150 ul | 15 ul | 3 mM |

TABLE 1-continued

Douncing Buffer Composition

| Douncing buffer reagents | Volume (50 ml) | (5 ml) | Final concentration |
|---|---|---|---|
| MgCl$_2$ (1M) | 100 ul | 10 ul | 2 mM |
| Triton X-100 (10%) | 500 ul | 50 ul | 0.1% |
| DTT (1M) ** | 25 ul | 2.5 ul | 0.5 mM |
| Halt Protease inhibitor (100x) ** | 500 ul | 50 ul | 1X |
| RNase inhibitor (20 U/ul) ** | 250 ul | 25 ul | 100 U/ml |

** Add these reagents fresh

Incubate for 5 min on ice and dounce 25 times using a dounce homogenizer.
Transfer the dounced nuclei to a 15 mL conical tube and centrifuge the nuclei.
Wash twice by resuspending the pellet in 5 mL douncing buffer and centrifuging.
Resuspend the pellet in storage buffer ($5\text{-}10 \times 10^6$ nuclei per 100 μL of storage buffer).

TABLE 2

Storage Buffer Composition

| Storage buffer reagents | Volume (5 ml) | (0.5 ml) | Final concentration |
|---|---|---|---|
| DEPC H$_2$O | 2.32 ml | 232 ul | |
| Tris-Cl pH 8.0 (1M) | 50 ul | 5 ul | 10 mM |
| Glycerol (50%) | 2.5 ml | 250 ul | 25% |
| MgAc$_2$ (1M) | 25 ul | 2.5 ul | 5 mM |
| EDTA (0.5M) | 1 ul | 0.1 ul | 0.1 mM |
| DTT (1M)** | 25 ul | 2.5 ul | 5 mM |
| Halt Protease inhibitor (100x)** | 50 ul | 5 | 1 |
| RNase inhibitor (20 U/ul)** | 25 ul | 2.5 ul | 100 ml |

**Add these reagents fresh

Proceed to nuclear run-on. If nuclear run-on is to be performed on a different day, flash freeze the nuclei in liquid nitrogen and store at −80° C. The nuclei in the storage buffer can be store at −80° C. for up to 5 years.

Cell Permeabilization.
Harvest adherent cells by scraping and centrifuging, non-adherent cells by centrifuging, and tissue samples by dissociating and preparing single cell suspension.
Resuspend the cell pellet in 10 mL ice-cold PBS and centrifuge.
Resuspend the cell pellet in ice-cold permeabilization buffer ($1 \times 10^6$ cells/mL).

TABLE 3

Permeabilitzation Buffer Composition

| Permeabilization buffer reagents | Volume (50 ml) | (5 ml) | Final concentration |
|---|---|---|---|
| DEPC H$_2$O | 31.5 ml | 3.150 ml | |
| Tris-Cl pH 7.4 (1M) | 500 ul | 50 ul | 10 mM |
| Sucrose (1M) | 15 ml | 1.5 ml | 300 mM |
| KCl (4M) | 125 ul | 12.5 ul | 10 mM |
| MgCl$_2$ (1M) | 250 ul | 25 ul | 5 mM |
| EGTA (500 mM) | 100 ul | 10 ul | 1 mM |
| Tween-20 (2%) | 1.25 ml | 125 ul | 0.05% |

TABLE 3-continued

Permeabilitzation Buffer Composition

| Permeabilization buffer reagents | Volume (50 ml) | Volume (5 ml) | Final concentration |
|---|---|---|---|
| Nonidet P-40 (10%) | 500 ul | 50 ul | 0.1% |
| DTT (1M) ** | 25 ul | 2.5 ul | 0.5 mM |
| Halt Protease inhibitor (100x) ** | 500 ul | 50 ul | 1X |
| RNase inhibitor (20 U/ul) ** | 250 ul | 25 ul | 100 U/ml |

** Add these reagents fresh

- Incubate for 5 min on ice and centrifuge the permeabilized cells.
- Wash twice by resuspending in 5 mL permeabilization buffer and centrifuging.
- Resuspend the cell pellet in storage buffer (5-10×10$^6$ permeabilized cells per 100 μL of storage buffer).
- Proceed to nuclear-run on. If nuclear run-on is to be performed on a different day, flash freeze the permeabilized cells in liquid nitrogen, and store in −80° C. The permeabilized cells in storage buffer can be stored at −80° C. for up to 5 years.
- Nuclear Run-on.
- Prepare a 2× nuclear run-on (NRO) master mix for 50 μL nuclei volume. Final volume of reaction is 100 μL.

TABLE 4

Nuclear run-on Master Mix Composition

| Reagents | Volume per 50 ul reaction (ul) | Final concentration − 1x (100 ul reaction) (mM) |
|---|---|---|
| Tris-Cl pH 8.0 (1M) | 0.5 | 5 |
| MgCl$_2$ (1M) | 0.25 | 2.5 |
| DTT (0.1M) | 0.5 | 0.5 |
| KCl (4M) | 5 | 200 |
| 3'O-Propargyl-ATP (1 mM) | 2.5 | 25 uM |
| 3'O-Propargyl-CTP (1 mM) | 2.5 | 25 uM |
| 3'O-Propargyl-GTP (1 mM) | 2.5 | 25 uM |
| 3'O-Propargyl-UTP (1 mM) | 2.5 | 25 uM |
| 2% sarkosyl | 1.25 | 0.025% |
| RNase inhibitor (20 U/ul) | 1 | (0.2 U/ul) |
| DEPC H$_2$O | 31.5 | |

- Preheat 50 μL of the 2× reaction mix to 37° C.
- Add 50 μL permeabilized cells (in storage buffer) to 50 μL of preheated 2× reaction mix, gently but thoroughly pipette the reaction 15 times, and place in a heat block at the appropriate temperature.
- Incubate for 3 min with gentle tapping at the incubation midpoint.
- Place the reaction on ice.
- Centrifuge the cells at 500 g for 2 min at 4° C.
- Remove the supernatant and wash permeabilized cells three times with 150 μL resuspension buffer.

TABLE 5

Resuspension Buffer Composition

| Resuspension buffer | Volume (50 ml) | Volume (5 ml) | Final conc. |
|---|---|---|---|
| DEPC H$_2$O | 46 ml | 4.6 ml | |
| Tris-Cl pH 8.0 (1M) | 250 ul | 25 ul | 5 mM |
| Glycerol (50%) | 2.5 ml | 250 ul | 2.5% |
| MgAc$_2$ (1M) | 12.5 ul | 12.5 ul | 2.5 mM |
| MgCl$_2$ (1M) | 62.5 ul | 6.25 ul | 1.25 mM |
| KCl (4M) | 750 ul | 75 ul | 60 mM |
| DTT (1M) ** | 150 ul | 15 ul | 3 mM |
| Halt Protease inhibitor (100x) ** | 100 ul | 10 ul | 0.2X |
| SUPERase inhibitor (20 U/ul) ** | 50 ul | 5 ul | 20 U/ml |

** Add these reagents fresh

- Resuspend in 1 mL resuspension buffer per 50 μL permeabilized cells.
- Pass the resuspended cells through the strainer of fluorescence-activated cell sorting (FACS) tubes.
- Take the filtered run-on cells in resuspension buffer and urea plates to the FACS facility for sorting cells into 96-well plates.
- Prepare 96-well plates and pipette 5 μL of 8M urea in each well using an Avidien 96-well pipettor.
- Single-Cell Sorting.
- Pipette 8M urea into 96-well plates using a 96-well pipettor (5 μL per well).
- Perform single cell sorting of run-on cells in 8M urea containing 96-well plates using FACS.
- If the copper(I)-catalyzed alkyne-azide cycloaddition (CuAAC) reaction is to be performed on a different day, seal the sorted plates with hot-press aluminum foil (180° C. for 2.5 seconds), and store the plates in −80° C.
- CuAAC Reaction.
- Prepare a mastermix plate of sodium ascorbate/PEG8000 (use multi-channel pipette), CuSO$_4$/BTTAA (use multi-channel pipette), and azide-single cell (sc)-barcode adaptor (use Avidien 96-well pipettor). For more than one plate, scale-up reactions accordingly.

TABLE 6

CuAAC Reaction Composition

| Reagents | Volume (μl) |
|---|---|
| Sodium ascorbate/PEG8000 (1.33M/25%) | 9 |
| azide-sc-barcode adaptor (1 μM) | 0.4 |
| CuSO$_4$/BTTAA (25 mM/125 mM) | 0.6 |

- Mix the reactions 9 times using Avidien tips used to add azide-sc-barcode adaptor.
- Discard the Avidien tips (mixing PEG causes bubbles to remain in the tips).
- Load new Avidien pipette tips.
- Aspirate 10 μL of the mastermix and dispense into 96-well plate containing 5 μL of 8M urea and single cells.
- Seal with hot-press aluminum foil (180° C. for 2.5s).
- Briefly centrifuge to collect samples at the center of each wells.
- Incubate the plates in shaking incubator at 65° C. for 1 hour (hr).
- Harvest CuAAC Reactions.
- Prepare 8 1.5-mL Eppendorf tubes per plate.
- Using the adjustable multichannel pipette, collect the reactions from the 96-well plate into the Eppendorf tubes using multi-aspirate mode.
- Add 15 μL of 5 mM EDTA (to chelate copper) to the empty plate with the Avidien 96-well pipettor.

Rinse the wells of the plate by rotating the liquid around the wells via tapping and pool the rinsed liquid.
Vortex and centrifuge briefly.
Transfer the pooled CuAAC reactions and rinsed solution into a 15 mL conical tube.
PEG8000 Removal by Trizol.
Add 3 mL Trizol to ~3 mL CuAAC reaction.
Vortex for 5 s.
Add 600 μL chloroform, vortex for 15 s, and incubate for 2 min at room temperature.
Centrifuge at 4,000 g for 5 min.
Transfer the aqueous layer to a clean microfuge tube.
Add 4 mL chloroform to remove mixed phenol and salts present in the CuAAC reaction.
Centrifuge at 4,000 g for 5 min.
Transfer the aqueous layer to ultracentrifugation columns.
Reaction Clean-Up.
Transfer the reaction into an ultracentrifugation column (Amicon, EMD Millipore, 3 kDa).
Bring the volume in the ultracentrifugation column to 5 mL using diethyl pyrocarbonate water (DEPC $H_2O$).
Centrifuge in a swinging bucket centrifuge at 4000 g for 40 min.
Discard the elute.
Bring the volume of the remaining reaction to 5 mL using DEPC $H_2O$.
Centrifuge in a swinging bucket centrifuge at 4000 g for 30 min.
Discard the elute.
Bring the volume of the remaining reaction to 5 mL using DEPC $H_2O$.
Centrifuge in a swinging bucket centrifuge at 4000 g for 25 min.
Discard the elute.
Transfer the remaining reaction from the ultracentrifugation column to a new Eppendorf tube.
Rinse the interior of ultracentrifugation column with 500 μL DEPC $H_2O$ and pool.
Add 2 μL of SUPERase Inhibitor to each sample.
Lyophilize the reaction to 72 μL in a SpeedVac.
RNA Fragmentation.
Prepare RNA fragmentation reactions as below:

TABLE 7

RNA fragmentation Reaction Composition

| Reagents | Volume (μL) |
| --- | --- |
| Lyophilized CuAAC reaction | 72 |
| $ZnCl_2$ (100 mM) | 9 |
| Tris, pH 7.0 (100 mM) | 9 |

Perform $ZnCl_2$ fragmentation using a heat block at 65° C. for 12 min.
Stop the reaction by adding 10 μL of 0.5M EDTA pH 8.0 (final conc. 50 mM EDTA, pH 8.0).
Mix and place on ice.
Purify the samples using Zymo Oligo Clean & Concentrator:
　Add 2× volume of Oligo Binding Buffer
Add 8× volume of 100% ethanol (EtOH) and mix briefly by pipetting.
Transfer the mixture to a provided Zymo-Spin column in a collection tube.
Centrifuge at 10,000 g for 30 seconds and discard the flow-through.
Add 750 μL DNA Wash Buffer to the column.
Centrifuge at 10,000 g for 30 second and discard the flow through.
Repeat wash with 750 μL DNA Wash Buffer.
Centrifuge at 14,000 g for 1 minute to elute residual wash buffer.
Transfer the column to a clean microcentrifuge tube.
Add 25 μL DEPC $H_2O$ directly to the column matrix.
Centrifuge at 14,000 g for 1 min to elute the oligonucleotide.
Lyophilize the purified sample to 5 μL.
Reverse Transcription.
Make reverse transcription (RT) primer mix:

TABLE 8

Reverse Transcription Primer Mix Composition

| Reagents | Volume (μL) |
| --- | --- |
| CuAAC reaction | 5 |
| RT primer RP1 (10 μM) | 1 |
| dNTP mix (10 mM) | 1 |

Add 2 μL of the RT primer mix to the 5 μL of samples.
Heat to 65° C. for 5 min, chill on ice for 2 min, and briefly spin at 1,000 g for 30s.
Prepare the RT reaction mix:

TABLE 9

Reverse Transcription Reaction Composition

| Reagents | Volume (μL) |
| --- | --- |
| Template switching oligonucleotide (10 μM) | 1 |
| SUPERase inhibitor | 1 |
| PEG 8000 (50%) | 6 |
| 5X RT buffer | 4 |
| Maxima H Minus | 1 |

Add 13 μL of appropriate RT reaction mix to the 6.5 μL of RNA-primer mix and incubate for 5 min at RT.
Transfer the reaction 0.2 mL PCR tubes.
Reverse transcribe the RNA in PCR block using scGROseq_RT program:

TABLE 10

Reverse Transcription Reaction Protocol

| Cycle | Temperature (° C.) | Time (min.) | Purpose |
| --- | --- | --- | --- |
| 1 | 50 | 60 | RT and template-switching |
| 2 | 85 | 15 | Enzyme activation |
| 3 | 4 | Hold | Safe storage |

Transfer the reaction to a 1.5 mL tube and rinse the PCR tubes with 30 μL DEPC $H_2O$.
Purify the samples using Zymo Oligo Clean & Concentrator as above.
PCR Amplification.
Prepare a full-scale amplification PCR mix according to the table below:

TABLE 11

PCR Reaction Mix Composition

| Reagents | Volume (μL) |
| --- | --- |
| Lyophilized sample | 25 |
| 5X High Fidelity (HF) buffer | 10 |

TABLE 11-continued

PCR Reaction Mix Composition

| Reagents | Volume (μL) |
|---|---|
| Betaine (5M) | 10 |
| PCR primer - F (12.5 μM) | 1 |
| PCR primer (indexed) - R (12.5 μM) | 1 |
| dNTP mix (12.5 mM each) | 2 |
| Phusion polymerase | 1 |

Use the following thermal cycling for pre-amplification:

TABLE 12

PCR Reaction Protocol

| | Steps | Denature (95° C.) | Anneal (68° C.) | Extend (72° C.) |
|---|---|---|---|---|
| 1 | Initial denaturation | 1 min | | |
| 2 | 1st PCR cycle | 10 s | 15 s | 20 s |
| 3 | Additional PCR cycles | Go to step 2 for 15 times | | |
| 4 | Final extension | — | — | 5 min |
| 5 | Storage | 4° C. forever | | |

Bring the volume of the reactions to 100 μL.
Purify the samples using Zymo DNA Clean & Concentrator-5:
  Add 700 μL of DNA binding buffer to 100 μL sample. Mix briefly by vortexing.
  Transfer 800 μL of the mixture to a provided Zymo-Spin Column in a Collection Tube.
  Centrifuge for 30 seconds. Discard the flow-through.
  Add 200 μL DNA Wash Buffer to the column.
  Centrifuge for 30 s at 10,000 g. Discard the flow-through.
  Repeat the wash step.
  Transfer the column to a 1.5 mL microcentrifuge tube.
  Add 25 μL DEPC $H_2O$ directly to the column matrix and incubate at room temperature for 1 min.
  Centrifuge for 30 s to elute the DNA.
Lyophilize the elute to 5 μL.
Size-Selection by PAGE.
Prepare a 10% TBE PAGE gel:

TABLE 13

PAGE Gel Composition

| Reagents | Volume | Final concentration |
|---|---|---|
| DEPC-$H_2O$ | 23 mL | — |
| Acrylamide (30%) | 16.45 mL | 10% |
| TBE (5X) | 10 mL | 1x |
| APS (10%) | 500 μL | 0.1% |
| TEMED | 50 μL | |

Pre-run the gel for 15 min at 300V.
Add 1 μL 6×DNA loading dye to the 5 μL sample and 5 μL DNA ladder.
Run the gel at 300V until the lower dye (bromophenol blue) is at the bottom of the gel.
Pry apart the gel and stain with 1× SYBR Gold for 5 min with shaking.
During the staining, puncture the bottom of a sterile, nuclease-free 0.5 mL centrifuge tube using a 21-gauge needle (heated in a Bunsen burner flame) to create a hole in the bottom of the tube. Place the 0.5 mL microtube into a sterile, round-bottom nuclease-free 2 mL microtube.
After the staining is complete, visualize the gel on a Dark Reader transilluminator.
Using a clean razor, cut the gel from 150-500 bp (15 bp above the 135 bp PCR product from adaptor dimer).
Place the gel fragment into the 0.5 mL microtube.
Centrifuge the stacked tubes at 10,000 g for 2 min at room temperature to shred the gel through the holes into the 2 mL tube (there is no liquid at this point).
Add 500 μL gel elution buffer and incubate for 2 h in a rotating incubator at 37° C.
Spin down the gel pieces for 1 min at max speed in a benchtop centrifuge.
Transfer all liquid possible to a Spin-X filter.
Centrifuge the filter for 1 min at 7,500 g. Collect the filtrate.
Lyophilize the sample using a SpeedVac dryer and reduce the volume to 100 μL. If the volume decreases below 100 μL, bring the volume up to 100 μL by adding DEPC $H_2O$.
Purify the samples using a Zymo DNA clean & Concentrator-5 (as above).
Use 2 μL of the library for quantification using Qubit (dsDNA HS).
The expected concentration of the library is between 1 and 20 ng/L.
If required, dilute the samples to 5 ng/μL.
Send ~10 ng to a sequencing facility. If the libraries are barcoded, pool the barcoded libraries that are to be sequenced simultaneously.
High-Throughput Sequencing.
The library should be accurately quantified for optimal cluster formation. We recommend digital PCR for quantification of cluster-generating DNA molecules in the library. Many sequencing facilities provide this service with a small additional cost.

Example 1. Technical Benchmarks

Figure 1B:
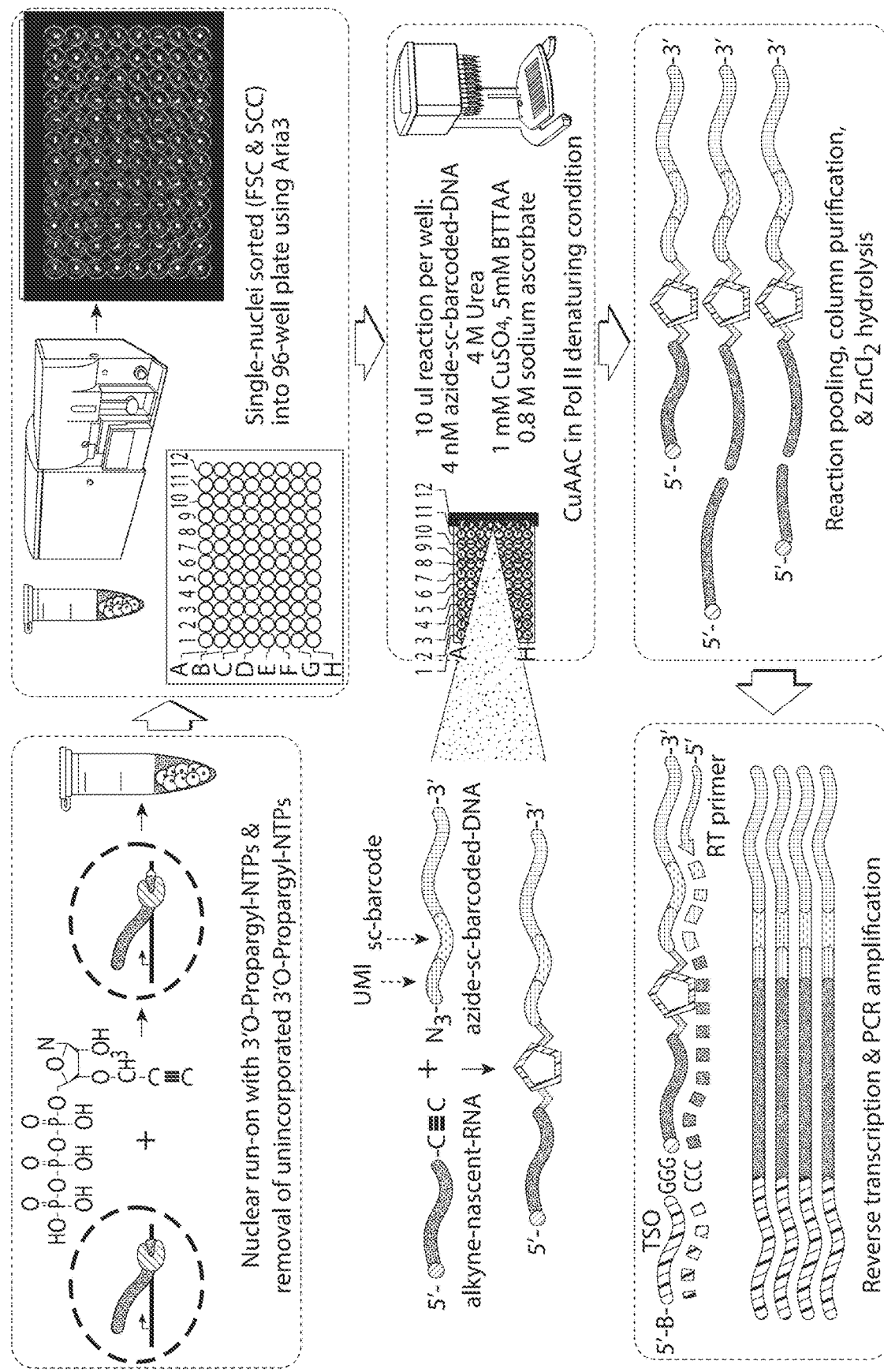

The protocol disclosed in the Materials and Methods for generating a scGROseq library from a single cell can be conducted using bead-bound single-cell barcode-adaptors (FIG. 1A) or free single-cell barcode-adaptors (FIG. 1B). The technical benchmarks that were achieved in labeling nascent RNA, labeling barcode-adaptors, conjugating nascent RNA to barcode-adaptors (RNA-barcoded-adaptor conjugates) using copper(I)-catalyzed alkyne-azide cycloaddition (CuAAC), release of propargyl-labeled nascent RNA, reverse transcription of RNA-barcoded-adaptor conjugates, incorporation of a second adaptor into RNA-barcoded-adaptor conjugates, forming barcode-adaptor hybrids, and conjugation of alkyne to all cellular RNAs for CuAAC-mediated capture.

Labeling Nascent RNA.

A nuclear run-on assay was conducted with single cells that had been solubilized with Sarkosyl (sodium lauroyl sarcosinate) in the presence of ATP, UTP, GTP, and either CTP or 3'O-propargyl-CTP. A Cy5-labeled azide was conjugated to the propargyl-labeled nascent RNA using CuAAC, wherein the copper source is $CuSO_4$ and copper (II) reducing agent is sodium ascorbate ($C_6H_7NaO_6$) (FIG. 2A). Conjugation of Cy5-labeled azide to propargyl-labeled nascent RNA confirms native RNA polymerase's ability to incorporate 3'O-propargyl-NTPs in nuclear run-on reaction (compare lanes 1, 3, and 4 to lanes 2, 5, and 6).

Figure 2B:
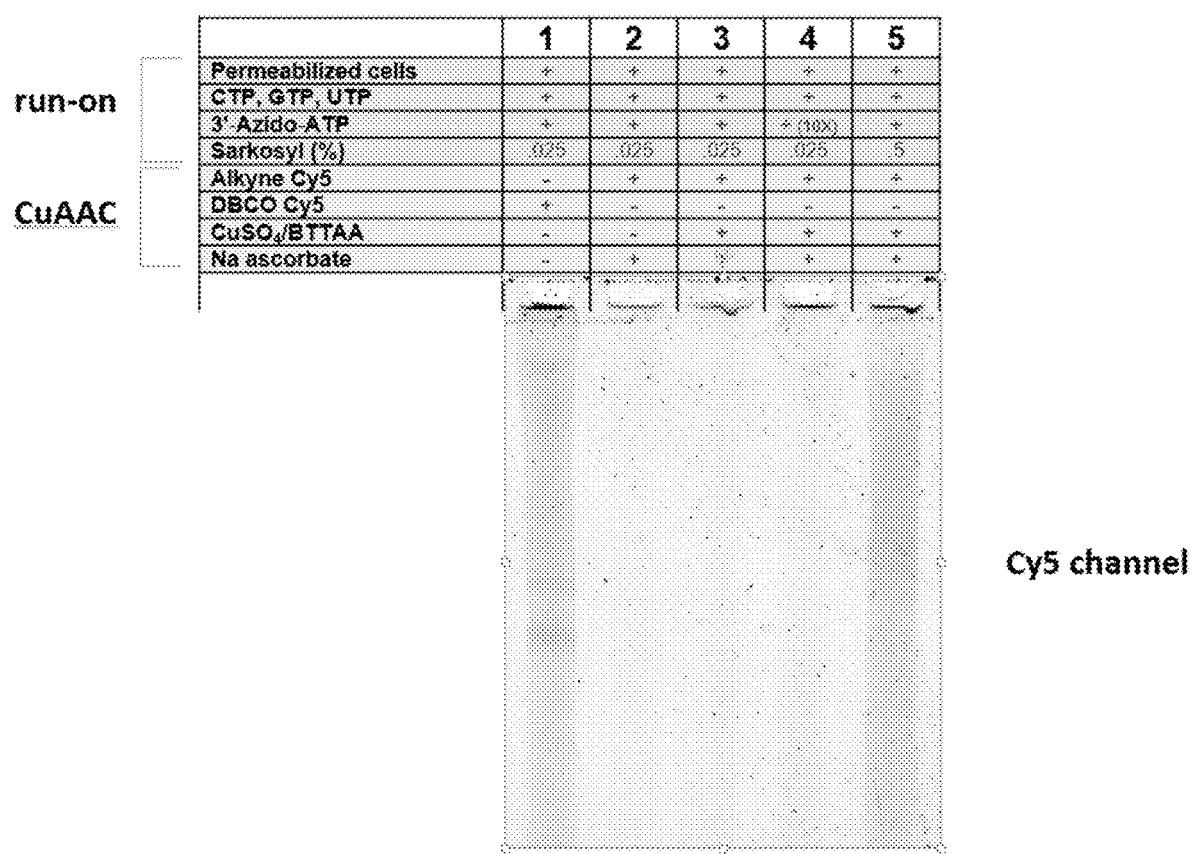
FIG. 2B shows the incorporation of 3'-azido-ATPs by native RNA polymerase. 3'-azido-ATP is incorporated into nascent RNA during a nuclear run-on assay in a nucleus solubilized with sodium lauroyl sarcosinate (Sarkosyl). 3'-azido-ATP nascent RNAs are conjugated to either Dibenzocyclooctyne-Cy5 (DBCO-Cy5) via strain-promoted azide-alkyne cycloaddition (SPAAC), or to Alkyne-Cy5 via CuAAC with $CuSO_4$ as the copper source, sodium ascorbate as the reducing agent for conversion of Cu(II) to Cu(I), and BTTAA as an accelerating ligand.

A second nuclear run-on assay was conducted with single cells solubilized in the presence of CTP, UTP, GTP, and either ATP or 3-azidoethyl-ATP. A Cy5-labeled alkyne (DBCO-Cy5) was conjugated to the azide-labeled nascent RNA using SPAAC, wherein the copper source is CuSO4, the copper (II) reducing agent is sodium ascorbate, and the accelerating ligand is BTTAA (FIG. 2B). Conjugation of Cy5-labeled alkyne to azide-labeled nascent RNA confirms native RNA polymerase's ability to incorporate 3-azido-ethyl-NTPs in nuclear run-on reaction and conjugation of azide-labeled nascent RNA to alkynes via SPAAC (compare lanes 1 and 5 to lanes 2, 3, and 4).

Labeling Single-Cell Barcode-Adaptors.

Figure 3A:
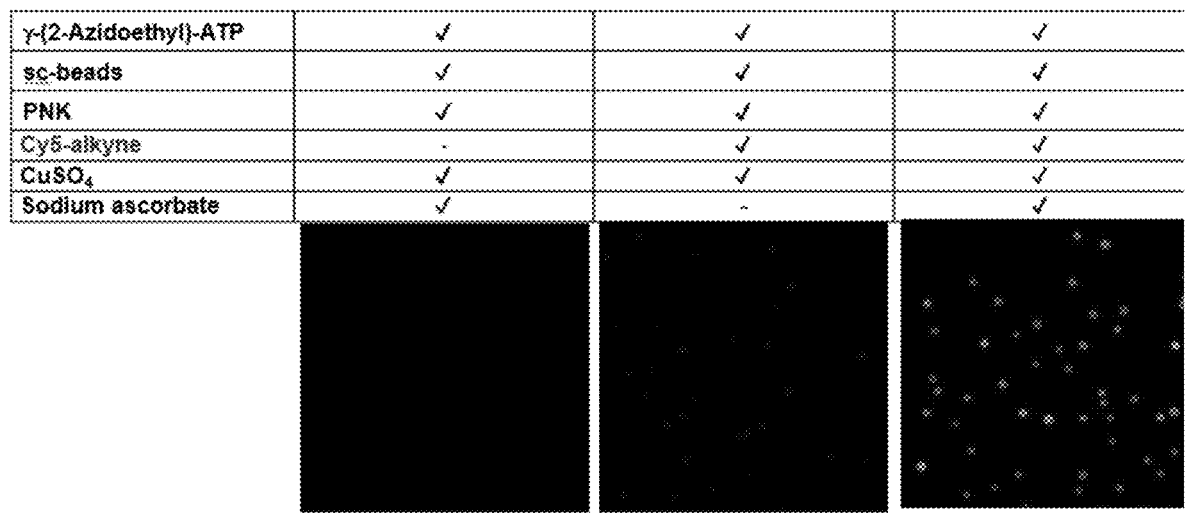
FIGS. 3A-3B show the transfer of azidoethyl to the 5'-end of bead-bound DNA. Polynucleotide kinase (PNK) catalyzes the transfer of azidoethyl from γ-(2-Azidoethyl)-ATP to the 5' end of DNA from a single cell bound to beads (sc-beads). Cy5-alkyne is conjugated to azidoethyl-sc-beads using Cu(I)-catalyzed Azide Alkyne Cycloaddition (CuAAC), with CuSO4 as the copper source and sodium ascorbate as the reducing agent for conversion of Cu(II) to Cu(I) (FIG. 3A). Azide-labeling of sc-barcoded beads is more efficient via iodine-conversion than PNK labeling (FIG. 3B).
Figure 3B:
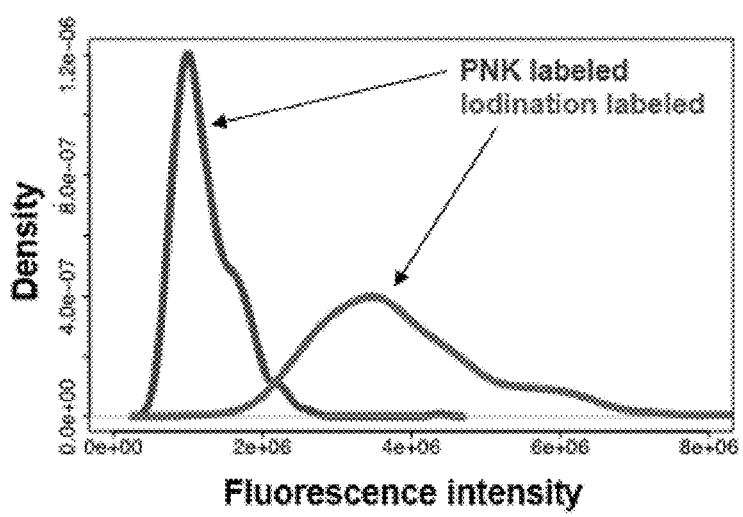

5' OH group in the bead-bound single-cell DNA barcodes (sc beads) were substituted with azidoethyl from γ-(2-azidoethyl)-ATP using polynucleotide kinase (PNK) (azide-labeled sc beads). To confirm the transfer of azidoethyl to sc beads, a Cy5-labeled alkyne was conjugated to the azide-labeled sc beads using CuAAC, wherein the copper source is CuSO4 and copper (II) reducing agent is sodium ascorbate ($C_6H_7NaO_6$) (FIG. 3A). Conjugation of Cy5-alkyne to azide-labeled sc beads confirms the azide-labeling of sc beads using PNK (compare lanes 1 and 2 to lane 3). Conversion of 5' Iodide to azide using sodium azide is more efficient than PNK-labeling. (FIG. 3B).

Conjugating Labeled-Nascent RNA to Labeled-Single-Cell Barcode-Adaptors.

Figure 4:
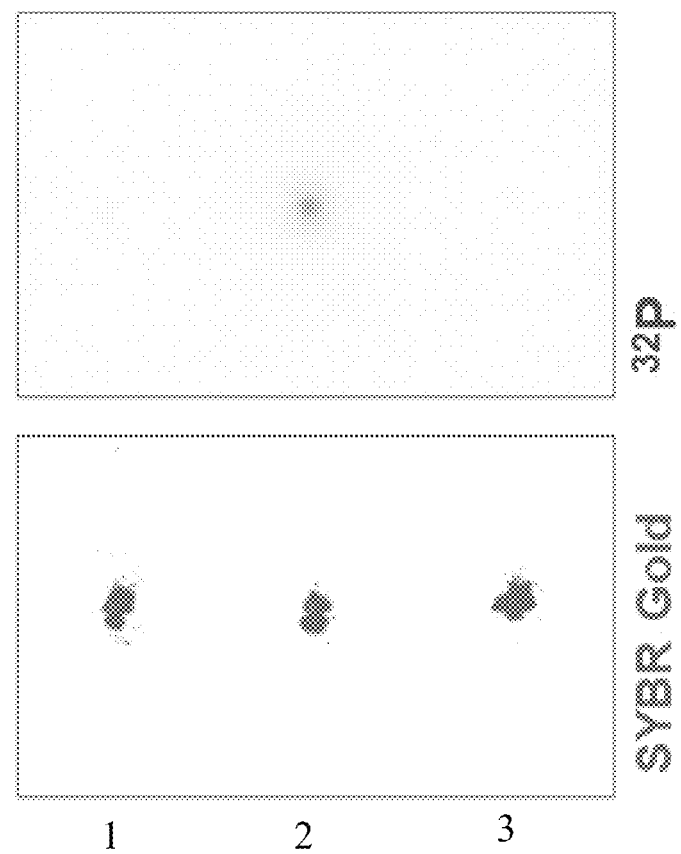
FIG. 4 shows the Cu(I)-catalyzed Azide Alkyne Cycloaddition (CuAAC) between RNA propargyl and azido-ethyl labeled single cell (sc)-barcoded beads. Propargyl-labeled RNA (propargyl-RNA) is labeled at the 5' end with γ-$^{32}$P ($^{32}$P-propargyl-RNA) by polynucleotide kinase (PNK). The $^{32}$P-propargyl-RNA is conjugated to azide-sc-beads using Cu(I)-catalyzed Azide Alkyne Cycloaddition (CuAAC) with $CuSO_4$ as the copper source and sodium ascorbate as the reducing agent for conversion of Cu(II) to Cu(I). SYBR Gold is a dye that detects nucleic acid.

RNA labeled with 3'O-propargyl (RNA-propargyl) was labeled with [γ-$^{32}$P]-ATP ($^{32}$P-ATP-RNA-propargyl) in the presence of polynucleotide kinase. Bead-bound azide-labeled single-cell DNA barcodes (azide-sc-beads) were conjugated to $^{32}$P-labeled RNA-propargyl using CuAAC, wherein the copper source is $CuSO_4$ and copper (II) reducing agent is sodium ascorbate ($C_6H_7NaO_6$) (FIG. 4). Conjugation of azide-sc-beads to ATP-RNA-propargyl requires PNK and sodium ascorbate (compare lanes 1 and 3 to lane 2).

Release of Propargyl-Labeled Nascent RNA.

The release of propargyl-labeled nascent RNA from polymerase II was evaluated using denaturants at the time of CuAAC conjugation. The propargyl-labeled RNA that was conjugated to azide-sc-beads was stained with fluorescent dye and the fluorescence was measured (data not shown). Trizol and 6M urea produced efficient release of propargyl-labeled RNA from polymerase II.

Reverse Transcription of RNA-Single-Cell-Barcoded-Adaptor Conjugates

Figure 5:
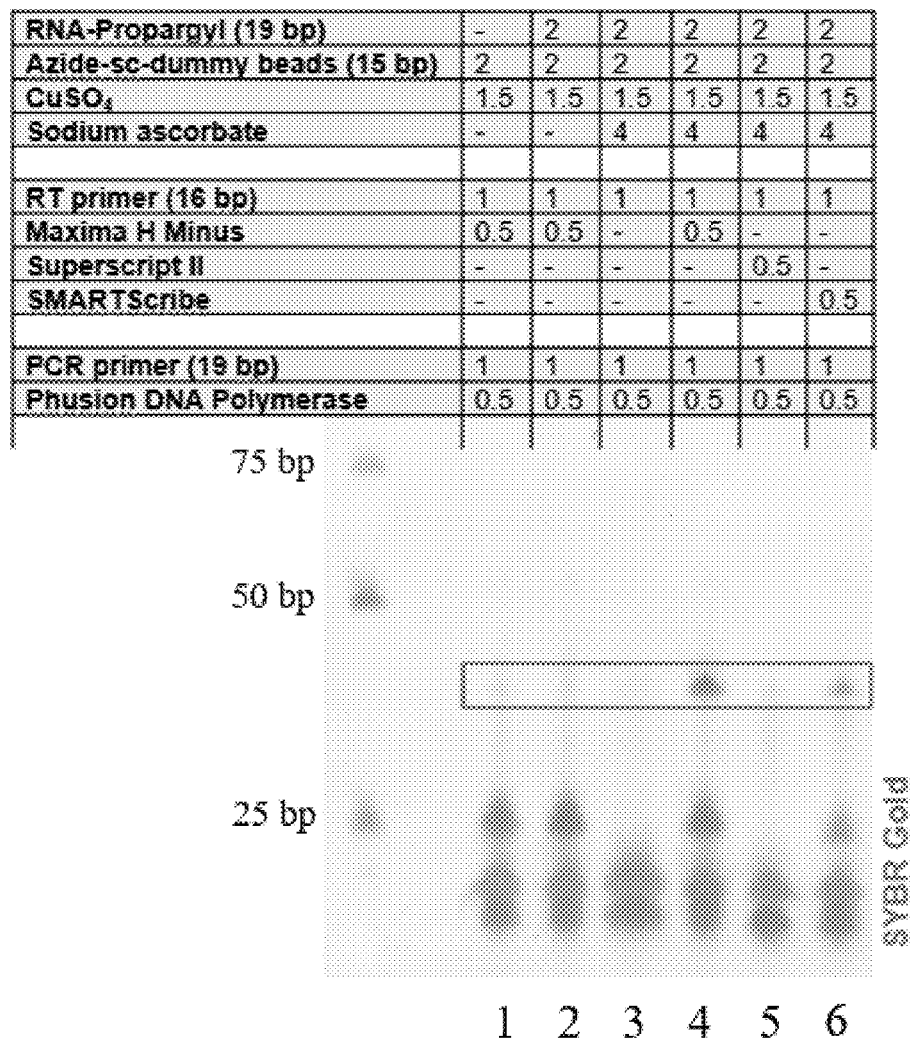
FIG. 5 shows reverse transcription of a RNA-single-cell-barcode-adaptor hybrid through a triazole ring. The single-cell barcode-adaptor was labeled with azide by converting iodine to azide at the 5' end of adaptor. A triazole ring is formed when propargyl-RNA is conjugated to bead-bound azido-ethyl labeled single cell barcode-adaptors, forming a RNA-single-cell-barcoded-adaptor conjugate. A reverse transcriptase (RT) primer is annealed to the RNA-single-cell-barcoded-adaptor conjugate. A RT polymerase extends the RT primer, producing complementary DNA (cDNA) that is complementary to the single cell barcode-adaptor, the triazole ring, and the RNA of the RNA-single-cell-barcoded-adaptor conjugate. The cDNA is then amplified by a polymerase chain reaction (PCR), and the expected PCR product is 38 base pairs (bp). SYBR Gold is a dye that detects nucleic acid.
Figure 6:
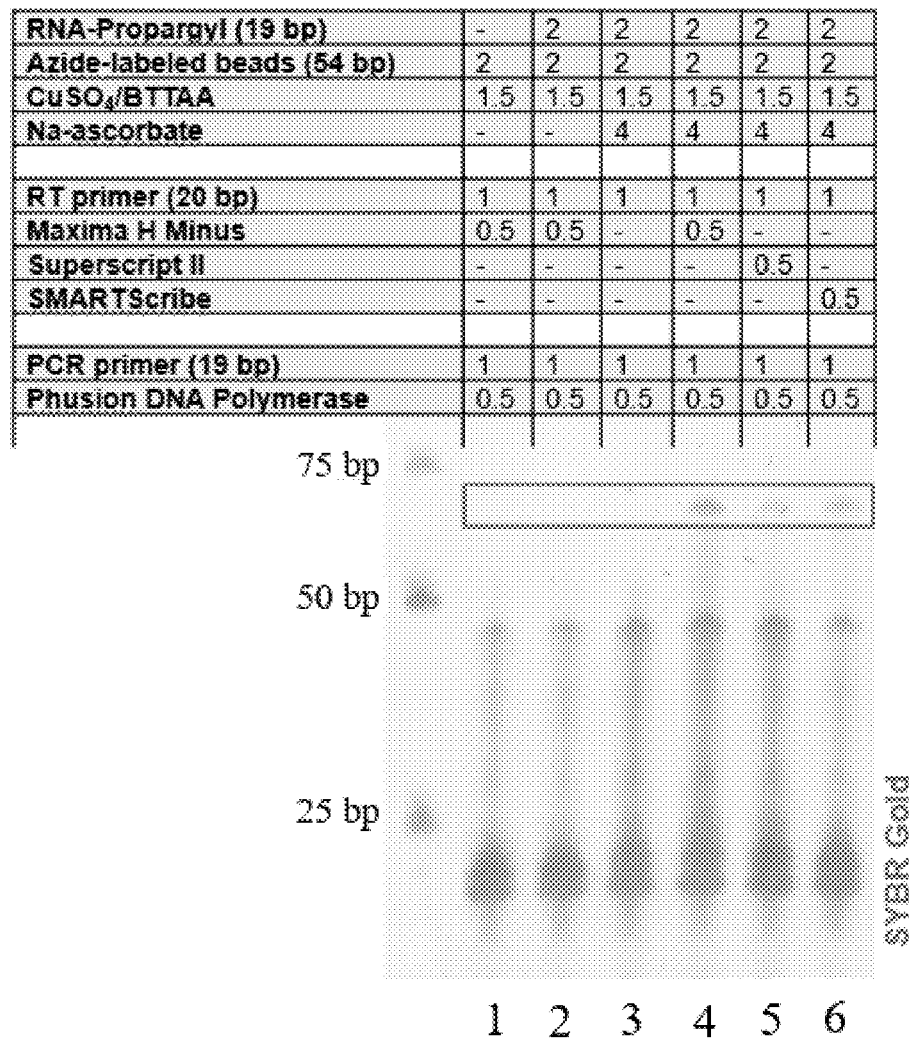
FIG. 6 shows reverse transcription of a RNA-single-cell-barcode-adaptor hybrid through a triazole ring. The single-cell barcode-adaptor was labeled with azide at the 5' end of the adaptor by PNK using γ-(2-Azidoethyl)-ATP. A triazole ring is formed when propargyl-RNA is conjugated to an azido-ethyl labeled single cell barcode-adaptor, forming a RNA-barcoded-adaptor conjugate. A reverse transcriptase (RT) primer is annealed to the RNA-single-cell-barcoded-adaptor conjugate. A RT polymerase extends the RT primer, producing complementary DNA (cDNA) that is complementary to the single cell barcode-adaptor, the triazole ring, and the RNA of the RNA-single-cell-barcoded-adaptor conjugate. The cDNA is then amplified by a polymerase chain reaction (PCR), and the expected PCR product is 65 base pairs (bp). SYBR Gold is a dye that detects nucleic acid.

A reverse transcriptase (RT) primer was annealed to propargyl-labeled RNA conjugated to an azide-labeled single-cell DNA bead (RNA-single-cell-barcoded-adaptor conjugate). The RT primer was complementary to the DNA. A RT polymerase (Maxima H Minus, Superscript II, or SMARTScribe) extended the RT primer to produce complementary DNA (cDNA). The cDNA was annealed by a PCR primer and amplified in the presence of Phusion DNA polymerase. The PCR products are then separated by size on a polyacrylamide gel electrophoresis (PAGE) gel (FIGS. 5-6). The Maxima H Minus RT polymerase appears to produce the most cDNA that can be amplified by PCR (compare lane 4 to lanes 5 and 6). Production of a detectable PCR product requires the propargyl-labeled RNA, sodium ascorbate, and an RT primer (compare lanes 1-3 to lanes 4-6).

Reverse Transcription of Single-Cell Barcode-Adaptor Hybrids

Figure 7:
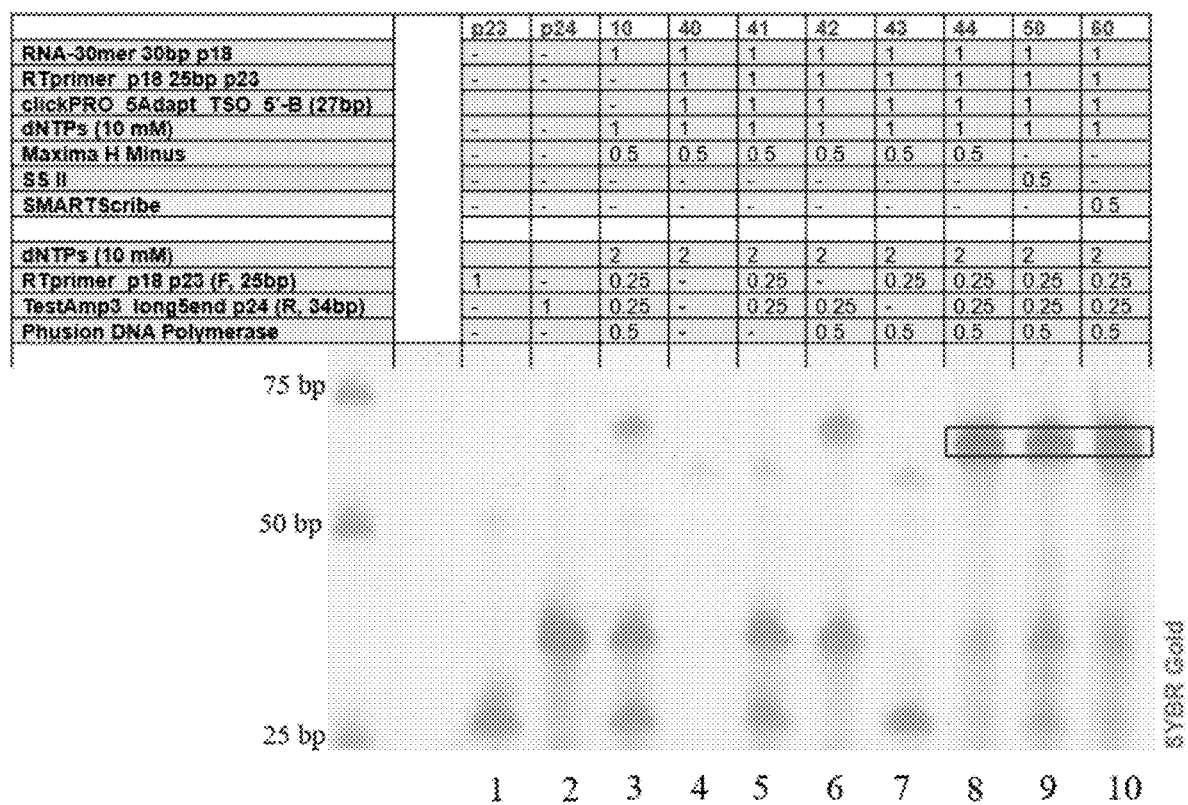
FIG. 7 shows incorporation of a second adaptor using template-switching oligonucleotide (TSO) for library preparation. A reverse transcription (RT) primer is complementary to alkyne-labeled RNA and is extended by reverse transcriptase to form complementary DNA (cDNA) with a "CCC" sequence at the 3' end as in FIG. 1A. A TSO containing a "GGG" sequence is annealed to the "CCC" sequence of the cDNA, which is further reverse transcribed by the reverse transcriptase and the reverse complement of the TSO sequence is added into the cDNA. This cDNA is then amplified by polymerase chain reaction (PCR), and the expected PCR product is 68 base pairs (bp). SYBR Gold is a dye that detects nucleic acid.

The RT primer, complementary to the RNA, was annealed to the RNA-single-cell-barcoded-adaptor conjugates. A RT polymerase (Maxima H Minus, Superscript II, or SMART-Scribe) extended the RT primer to produce complementary DNA (cDNA). A template switching oligonucleotide (TSO) was annealed to "CCC" portion of the cDNA. The cDNA was annealed by PCR primers and amplified in the presence of Phusion DNA polymerase. The PCR products are then separated by size on a polyacrylamide gel electrophoresis (PAGE) gel (FIG. 7). The Maxima H Minus, SuperScript II, and SMARTScribe RT primers appear to produce similar amounts of cDNA that can be amplified by PCR (compare lanes 8, 9 and 10). Thus, a TSO can be incorporated by the RT enzyme during RT of a clicked RNA-barcoded-adaptor conjugate.

Conjugation of Alkyne to all Cellular RNA for CuAAC-Mediated Capture.

Figure 8:
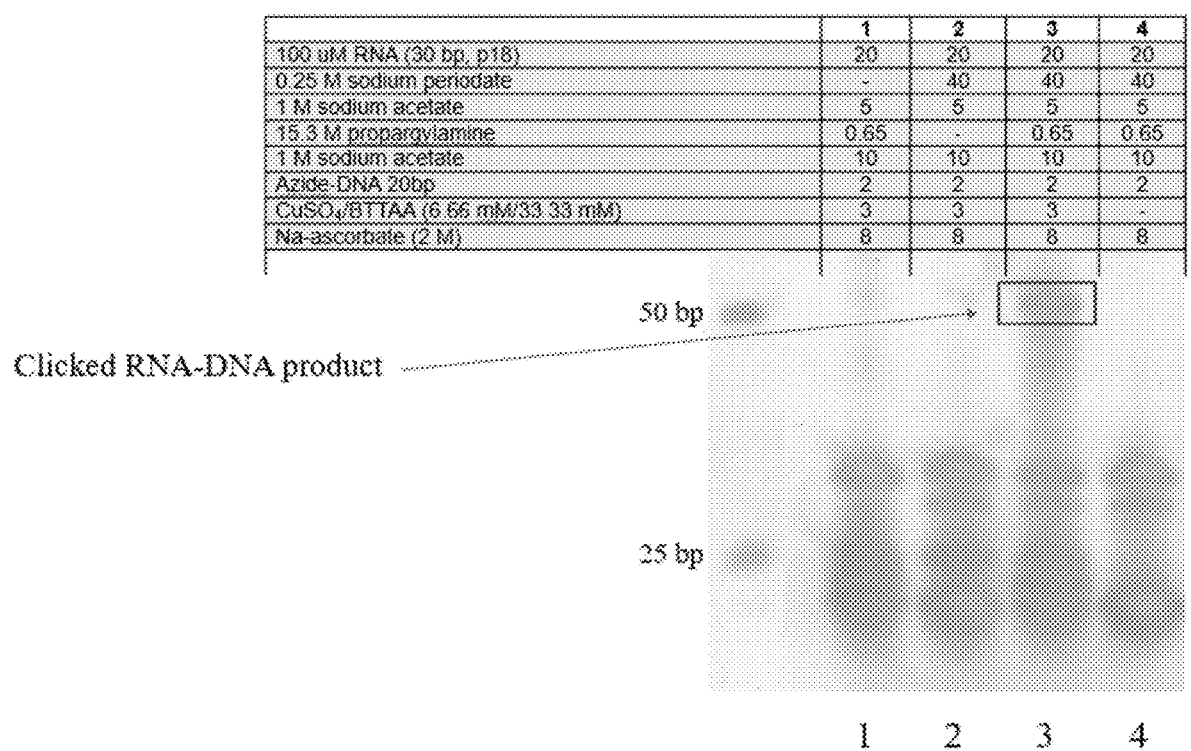
FIG. 8 shows conjugation of an alkyne to nascent cellular RNAs for Cu(I)-catalyzed Azide Alkyne Cycloaddition (CuAAC)-mediated capture. An alkyne (propargylamine) was conjugated to nascent cellular RNAs and single cell barcode-adaptors were modified with an azide group. The alkyne-RNA was conjugated to the azide-labeled single-cell barcode-adaptors using CuAAC (clicked RNA-DNA product). $CuSO_4$ is the copper source, Na-ascorbate is a reducing agent, and BTTAA is a CuAAC accelerating ligand. The clicked RNA-DNA product was 50 bp and was amplified by PCR.
Figure 9:
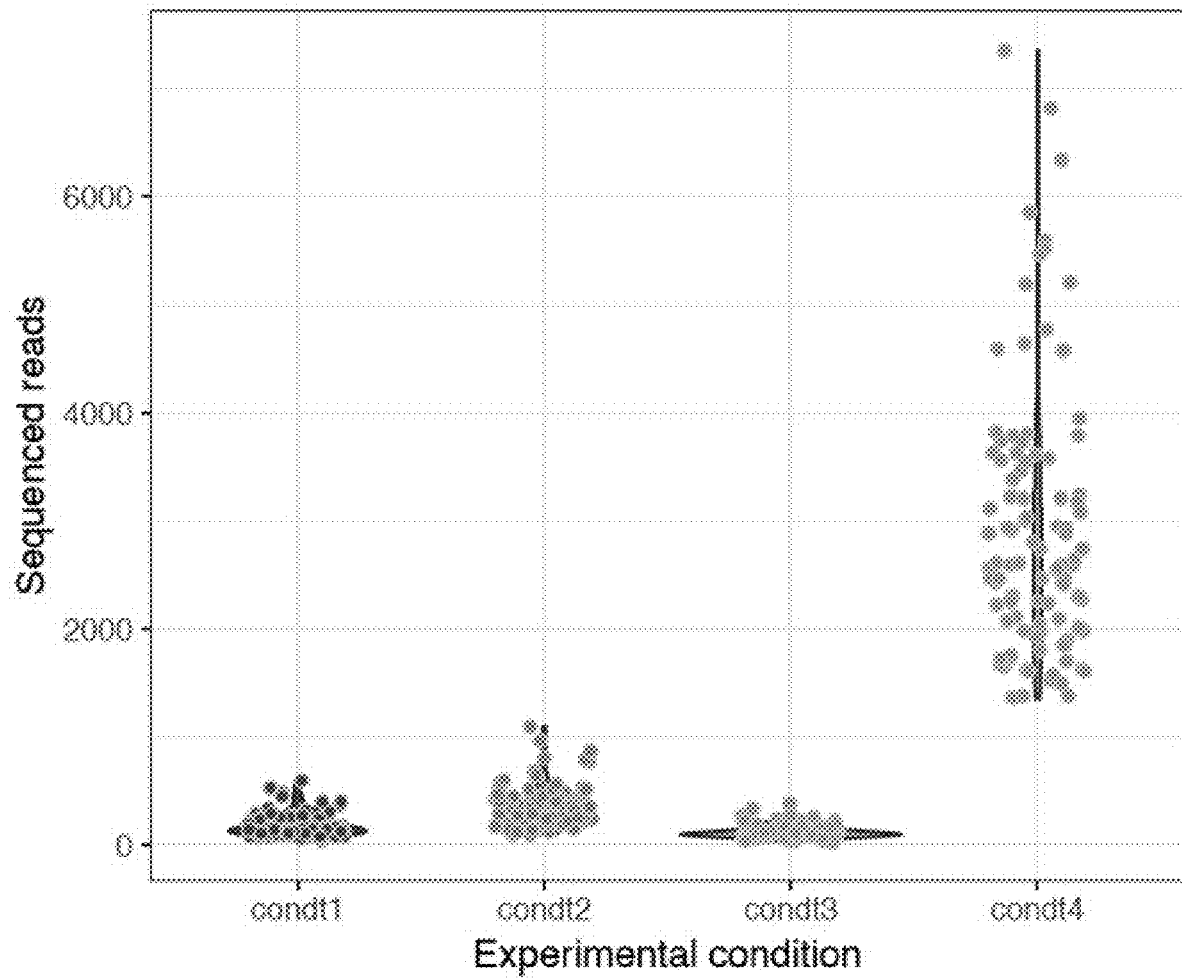
FIG. 9 shows the number of scGROseq reads sequenced in four conditions. Conditions 1, 2, 3, and 4 (condt1, condt2, condt3, condt4) are variations on a non-bead-based scGROseq protocol. Each dot represents a single cell.
Figure 10:
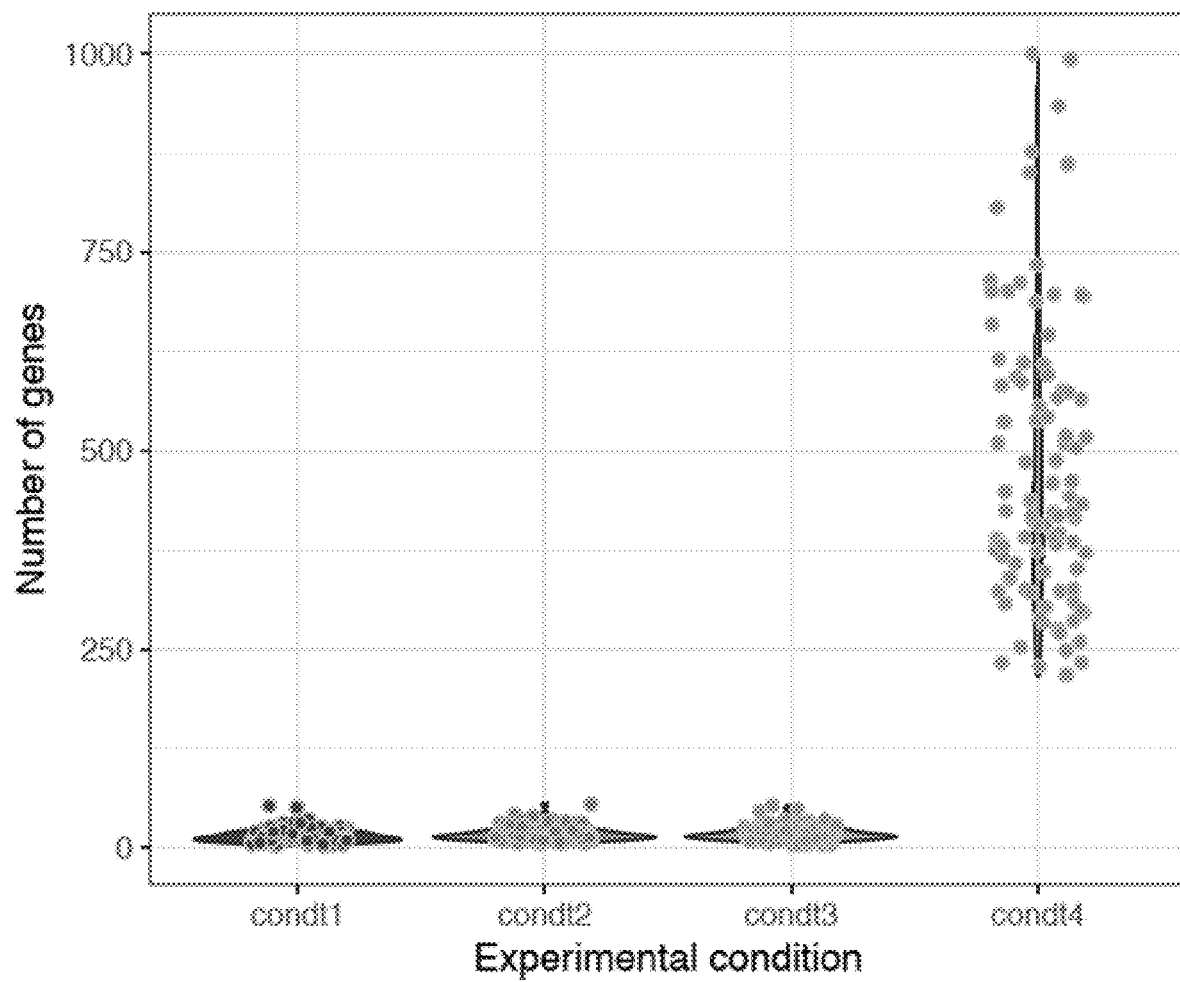
FIG. 10 shows the number of mouse genes identified in scGROseq libraries of four conditions. Conditions 1, 2, 3, and 4 (condt1, condt2, condt3, condt4) are variations on a non-bead-based scGROseq protocol. Each dot represents a single cell.
Figure 11A:
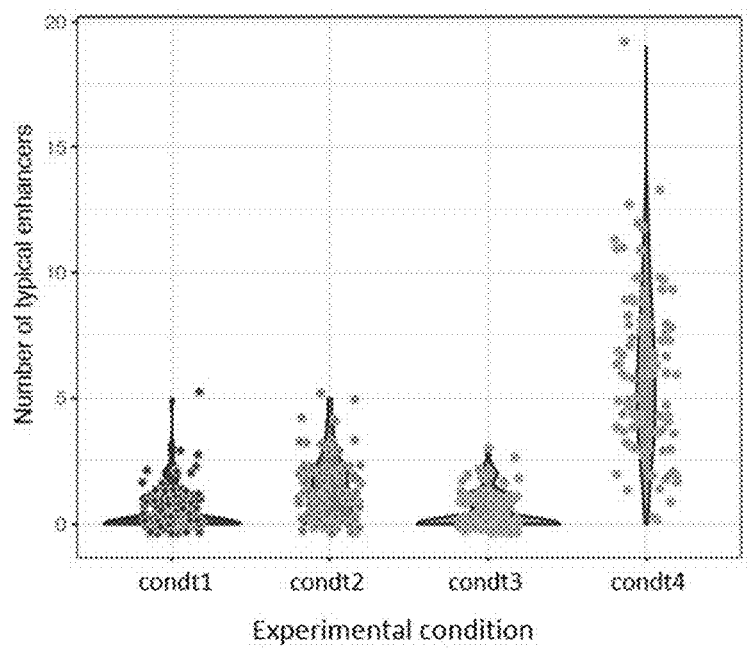
FIGS. 11A-11B show the number of enhancers (FIG. 11A) and super-enhancers (FIG. 11B) identified in scGROseq libraries of four conditions. Conditions 1, 2, 3, and 4 (condt1, condt2, condt3, condt4) are variations on a non-bead-based scGROseq protocol. Each dot represents a single cell.
Figure 11B:
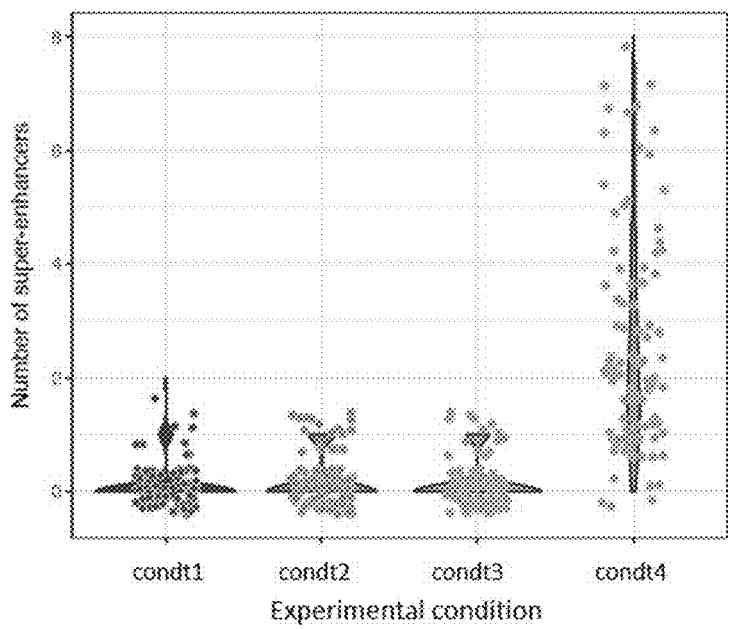

All cellular RNA was labeled with proparylagmine (prop-argylamine-RNA) in the presence of sodium periodate and sodium acetate. Azide-labeled DNA (azide-DNA) was conjugated to the propargylamine-RNA using CuAAC (RNA-single-cell-barcoded-adaptor conjugate), wherein the copper source is $CuSO_4$, the copper (II) reducing agent is sodium ascorbate ($C_6H_7NaO_6$), and the accelerating ligand is BTTAA (FIG. 8). Conjugation of propargylamine to RNA is feasible using sodium periodate, propargylamine, and CuSO4/BTTAA (compare lane 3 to lanes 1, 2, and 4).

Example 2. scGROseq Libraries Detect Genes and Enhancers scGROseq libraries were produced by the methods presented herein in the Materials and Methods and Example 1 from mouse cells. Four protocols with slight variations were used to produce scGROseq libraries. The scGROseq library produced using condition 4 (condt4) produced a greater number of sequenced reads, a greater number of genes detected, and a greater number of enhancers and super-enhancers than conditions 1-3 (condt1, condt2, condt3) (FIGS. 9-11B). All subsequent experiments were conducted with scGROseq libraries produced using the protocol of condition 4.

Figure 12:
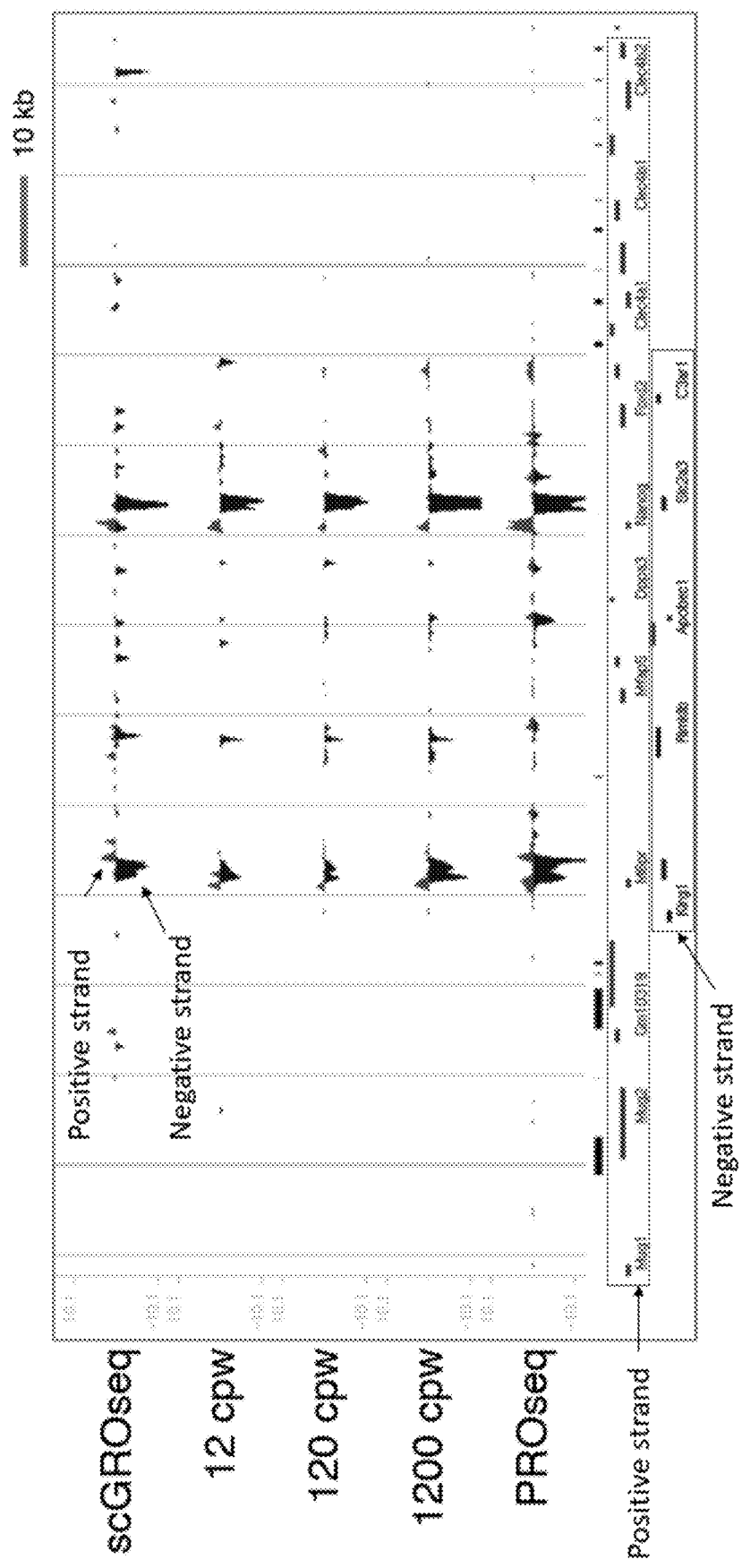
FIG. 12 shows a genome browser screen-shot of a region of mouse chromosome 6. The horizontal bars on the bottom of the panel are genes identified on the positive and negative strands of the genome. scGROseq indicates a single cell was present in each well of a 96-well plate, 12 cpw indicates 12 cells per well, 120 cpw indicates 120 cells per well, 1200 cpw indicates 1200 cells per well, and PROseq indicates a protocol for mapping the location of RNA polymerases in a cell with sequences from 5 million cells.
Figure 13A:
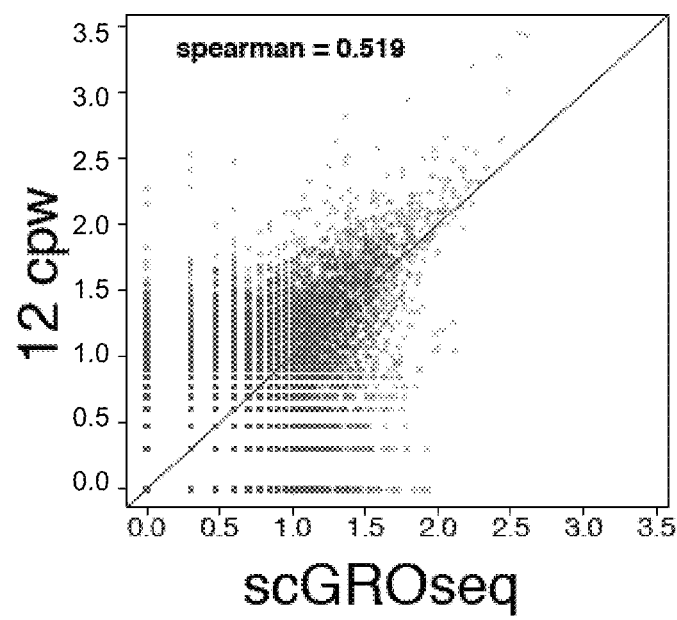
FIGS. 13A-13D show that scGROseq libraries correlate with libraries prepared with multi-cell and bulk-cell data. The number of genes present in each library is compared between scGROseq and 12 cells per well (FIG. 13A), scGROseq and 120 cells per well (FIG. 13B), scGROseq and 1200 cells per well (FIG. 13C), and scGROseq and PROseq (FIG. 13D). Each dot in the plots represents a gene. The data from 96 wells, each containing a single cell, were pooled for scGROseq.
Figure 13B:
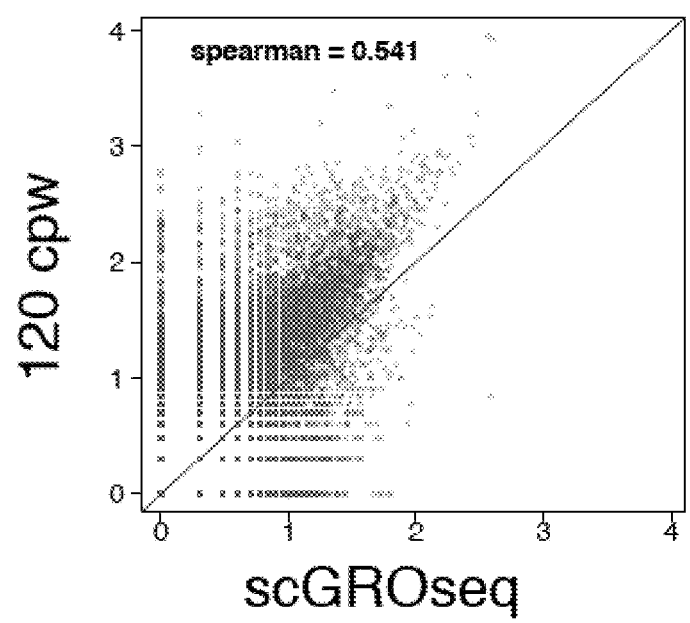
Figure 13C:
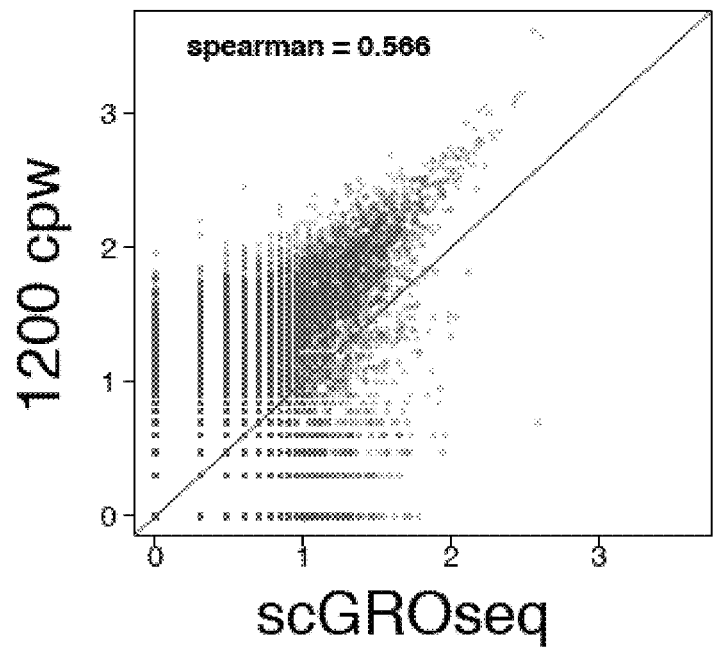
Figure 13D:
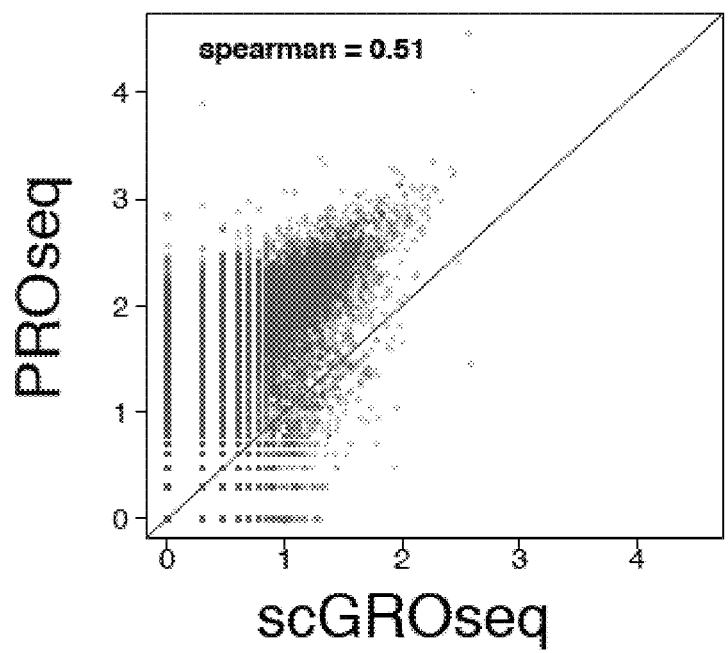
Figure 14A:
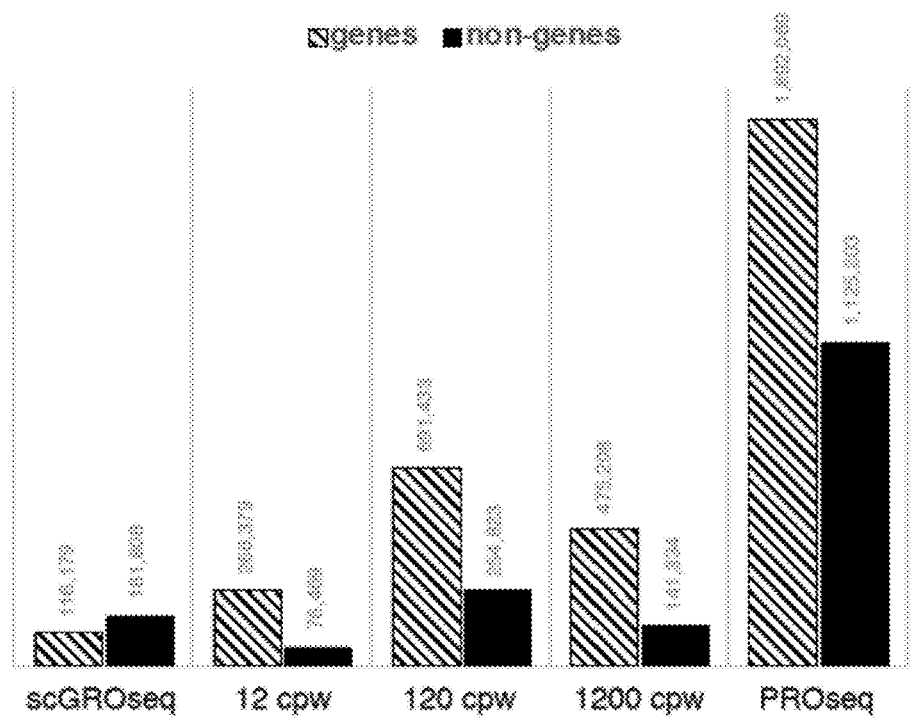
FIGS. 14A-14B show the number of scGROseq reads mapped to the mouse genome and the number of the mouse genes represented by scGROseq. The number of sequences mapped to genes in the mouse genome are shown using a single cell per well (scGROseq), 12 cells per well (12 cpw), 120 cells per well (120 cpw), 1200 cells per well (1200 cpw), and PROseq bulk data (PROseq) (FIG. 14A). The number of genes in the mouse genome that are retrieved are shown using scGROseq, 12 cpw, 120 cpw, 1200 cpw, or PROseq (FIG. 14B). The data from 96 wells, each containing a single cell, were pooled for scGROseq.
Figure 14B:
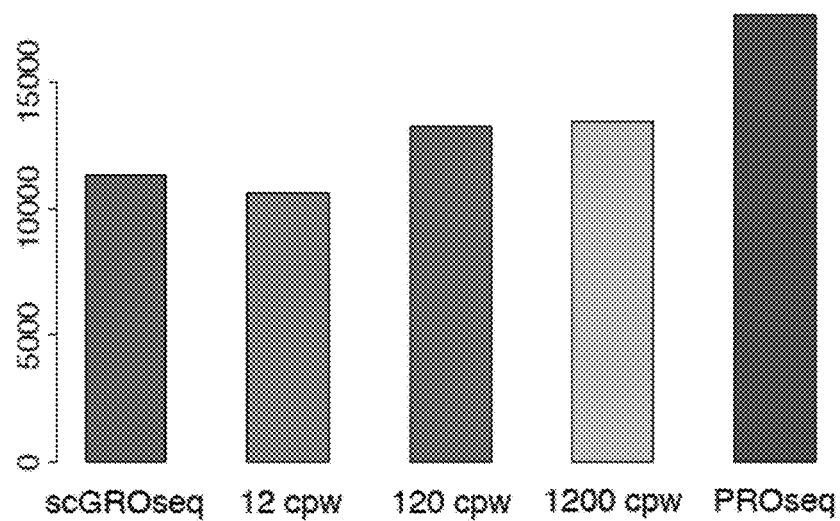
Figure 15:
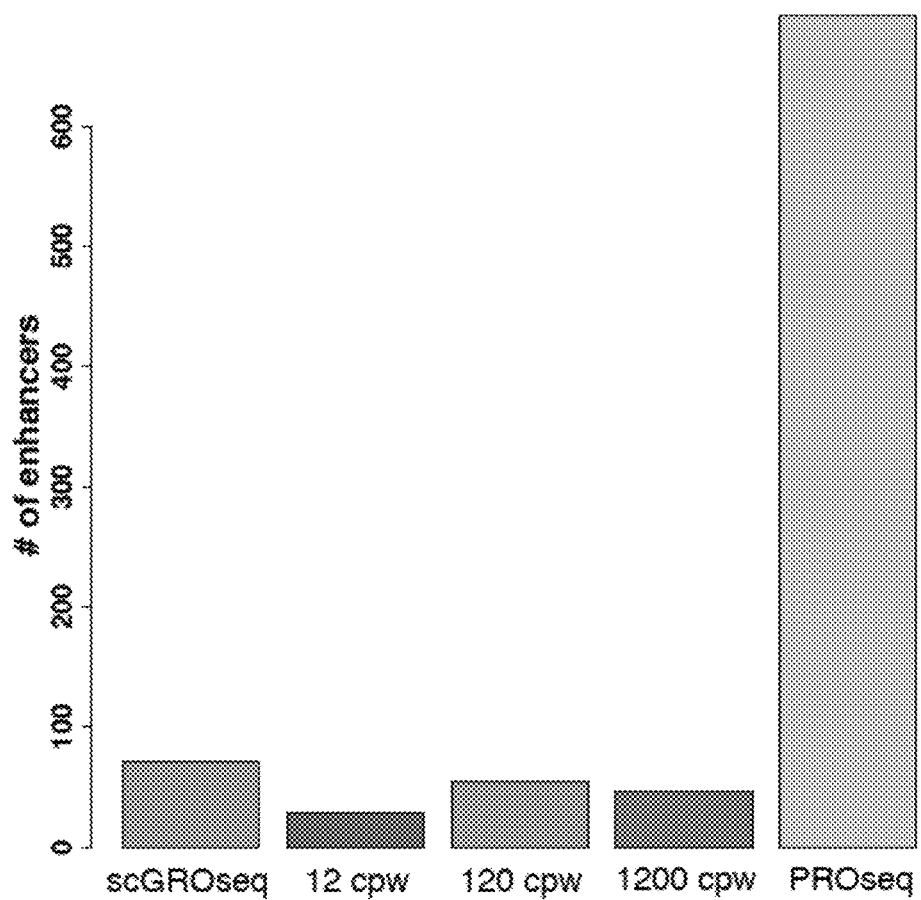
FIG. 15 shows the number of enhancers identified in a mouse genome using a single cell per well of a 96 well plate (scGROseq), 12 cells per well (12 cpw), 120 cells per well (120 cpw), 1200 cells per well (1200 cpw), and PROseq bulk data (PROseq).

The scGROseq library was compared to libraries generated using a higher number of cells. A region of mouse chromosome 6 was compared for the genes detected on both the positive and negative strands between scGROseq (1 cell per well), 12 cells per well (12 cpw), 120 cells per well (120 cpw), 1200 cells per well (1200 cpw), and bulk cell data (PROseq). The scGROseq library detects similar gene patterns on both the position and negative strands of mouse chromosome 6 compared to libraries generated using a higher number of cells (FIG. 12). Furthermore, the number of genes detected in the total scGROseq library is comparable to the number of genes detected in the 12 cpw, 120 cpw, 1200 cpw, and PROseq libraries (FIGS. 13A-13D, 14B), despite the fact that the total number of mapped sequences is lower (FIG. 14A). Additionally, the scGROseq library detects more enhancers than the 12 cpw, 120 cpw, and 1200 cpw libraries (FIG. 15).

Taken together, these results suggest that a nascent RNA scGROseq library produced using the methods described herein can detect genes, enhancers, and super-enhancers in a single cell. These libraries are particularly valuable because some nascent RNA (e.g., enhancer RNA, super-enhancer RNA) is rapidly degraded.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

What is claimed is:

1. A method for analyzing nascent RNA comprising:
   labeling nascent RNA in one or more permeabilized cells or nuclei by incubating the one or more permeabilized cells or nuclei with either alkyne-NTPs or azide-NTPs, which are incorporated into nascent RNA transcripts by RNA polymerases in the one or more permeabilized cells or nuclei;
   providing bead-bound or free azide-labeled single-cell barcode-adaptors if the one or more permeabilized cells or nuclei are incubated with alkyne-NTPs, or providing bead-bound or free alkyne-labeled singe-cell barcode-adaptors if the one or more permeabilized cells or nuclei are incubated with the azide-NTPs;
   contacting the lysate of the one or more permeabilized cells or nuclei with the bead-bound or free azide-labeled single-cell barcode-adaptor or the bead-bound or free alkyne-labeled single-cell barcode-adaptor in the presence of a copper-catalyzed azide-alkyne cycloaddition (CuAAC) reaction reagent, forming RNA-single-cell-barcoded-adaptor conjugates; and
   optionally, sequencing the nascent RNA or measuring the level of RNAs by quantitative PCR (qPCR).

2. The method of claim 1, wherein the azide group is at or near the 5'-end of the bead-bound single-cell barcode-adaptors or the free single-cell barcode-adaptors.

3. The method of claim 1, wherein the sequencing comprises annealing a reverse transcription primer to the bead-bound single-cell barcode-adaptors or free single-cell barcode-adaptors, and contacting the annealed reverse transcription primer with a polymerase to reverse transcribe the nascent RNA through an adduct formed by the CuAAC reaction.

4. The method of claim 3, wherein the adduct is a triazole ring.

5. The method of claim 3, further comprising incorporating a second adaptor, thereby forming a single-cell barcode-adaptor hybrid.

6. The method of claim 5, wherein the incorporation is by a template-switching oligonucleotide or ligation.

7. The method of claim 1, wherein the nascent RNA is sequenced from a single permeabilized cell or nucleus or a plurality of permeabilized cells or nuclei.

8. The method of claim 1, wherein:
(i) the CuAAC reaction reagent is copper sulfate (CuSO4), tetrakis(acetonitrile)copper(I)hexafluorophosphate ((Cu(CH3CN)4]PF6), tetrakis(acetonitrile) copper(I) triflate (Cu(CH3CN)4]OTf, copper acetate ($C_4H_6CuO_4$), copper bromide (BrCu), or copper iodide (CuI);
(ii) the reducing reagent reduces Cu(II) to Cu(I) in the CuAAC reaction, optionally wherein the reducing reagent is sodium ascorbate, hydrazine, tris(2-carboxyethyl)phosphine (TCEP), dithiothreitol (DTT), or beta-mercaptoethanol;
(iii) the CuAAC reaction is in the presence of an accelerating ligand, optionally wherein the accelerating ligand is 2-[4-({bis[(1-tert-butyl-1H-1,2,3-triazol-4-yl) methyl]amino]methyl) -1H-1,2,3-triazol-1-yl]lacetic acid (BTTAA), (1-(4-methoxybenzyl)-1-H-1,2,3-triazol-4-yl)methanol (MBHTM), or tris-hydroxypropyltriazolylmethylamine (THPTA); and/or
(iv) the CuAAC reaction is in the presence of a releasing agent, optionally wherein the releasing agent is urea.

9. The method of claim 1, further comprising sorting the one or more permeabilized cells or nuclei into single wells or encapsulated into aqueous droplets in oil emulsion.

10. A method for analyzing nascent RNA comprising:
labeling nascent RNA in one or more permeabilized cells or nuclei by incubating the one or more permeabilized cells or nuclei with azide-NTPs, which are incorporated into nascent RNA transcripts by RNA polymerases in the one or more permeabilized cells or nuclei;
providing bead-bound or free alkyne-labeled single-cell barcode-adaptors;
contacting a lysate of the one or more permeabilized cells or nuclei with the bead-bound or free alkyne-labeled single-cell barcode-adaptors in the presence of a strain-promoted azide-alkyne cycloaddition (SPAAC) reaction reagent, forming RNA-single-cell-barcoded-adaptor conjugates; and
optionally, sequencing the nascent RNA or measuring the level of RNAs by quantitative PCR (qPCR).

11. The method of claim 10, wherein the sequencing comprises annealing a reverse transcription primer to the bead-bound single-cell barcode-adaptors or free single-cell barcode-adaptors, and contacting the annealed reverse transcription primer with a polymerase to reverse transcribe the nascent RNA through an adduct formed by the SPAAC reaction.

12. The method of claim 11, wherein the adduct is a triazole ring.

13. The method of claim 10, further comprising incorporating a second adaptor, thereby forming a single-cell barcode-adaptor hybrid.

14. The method of claim 13, wherein the incorporation is by a template-switching oligonucleotide or ligation.

15. The method of claim 10, wherein the nascent RNA is sequenced from a permeabilized single cell or nucleus.

16. The method of claim 10, wherein the nascent RNA is sequenced from a plurality of permeabilized cells or nuclei.

17. The method of claim 10, wherein the alkyne is bicyclo[6.1.0]nonyne (BCN), N-[(1R,8S,9s)-bicyclo[6.1.0] non-4-yn-9-ylmethyloxycarbonyl]-1,8-diamino-3,6-dioxaoctane, (1R,8S,9s)-bicyclo[6.1.0]non-4-yn-9-ylmethanol, or [(1R,8S,9s) -bicyclo[6.1.0]non-4-yn-9-ylmethyl N-succinimidyl carbonate.

18. A method for analyzing RNAs in a permeabilized cell or nucleus comprising:
transferring an azide or an alkyne group to the gamma (γ) phosphate on the 5' end of the RNAs;
isolating the RNAs; and
optionally sequencing the RNAs; or measuring the level of RNAs by quantitative PCR (qPCR).

19. The method of claim 18, wherein the transferring is catalyzed by:
(i) polynucleotide kinase; or
(ii) ligation or hybridization of a small oligonucleotide containing azide or alkyne.

* * * * *

UNITED STATES PATENT AND TRADEMARK OFFICE
CERTIFICATE OF CORRECTION

PATENT NO. : 11,519,027 B2
APPLICATION NO. : 16/368957
DATED : December 6, 2022
INVENTOR(S) : Phillip A. Sharp et al.

It is certified that error appears in the above-identified patent and that said Letters Patent is hereby corrected as shown below:

In the Claims

In Claim 8, at Column 35, Line 18:
"methyl]amino]methyl)-1H-1,2,3-triazol-1-yl]lacetic"
Should read:
"methyl]amino}methyl)-1H-1,2,3-triazol-1-yl]acetic"

Signed and Sealed this
Fourteenth Day of March, 2023

Katherine Kelly Vidal
*Director of the United States Patent and Trademark Office*